(12) United States Patent
Hahn et al.

(10) Patent No.: US 8,451,440 B2
(45) Date of Patent: May 28, 2013

(54) APPARATUS FOR THE OPTICAL INSPECTION OF WAFERS

(75) Inventors: Kurt Hahn, Giessen (DE); Roland Hedrich, Ehringshausen (DE); Gerhard Hoppen, Wetzlar (DE); Lambert Danner, Wetzlar (DE); Albert Kreh, Solms (DE); Wolfgang Vollrath, Burbach (DE); Alexander Büttner, Weilburg (DE); Christof Krampe-Zadler, Castrop-Rauxel (DE); Henning Backhauss, Wetzlar (DE); Hermann Bittner, Limburg (DE)

(73) Assignee: Kla-Tencor Mie GmbH, Weilburg (DE)

( * ) Notice: Subject to any disclaimer, the term of this patent is extended or adjusted under 35 U.S.C. 154(b) by 604 days.

(21) Appl. No.: 12/716,612

(22) Filed: Mar. 3, 2010

(65) Prior Publication Data

US 2010/0295938 A1   Nov. 25, 2010

(30) Foreign Application Priority Data

May 19, 2009   (DE) .......................... 10 2009 025 831
Sep. 30, 2009   (DE) .......................... 10 2009 044 151

(51) Int. Cl.
*G01N 21/00* (2006.01)
*G01N 21/95* (2006.01)

(52) U.S. Cl.
CPC .................................. *G01N 21/9501* (2013.01)
USPC .................................................... 356/237.2

(58) Field of Classification Search
None
See application file for complete search history.

(56) References Cited

U.S. PATENT DOCUMENTS

| 5,674,698 | A  | * | 10/1997 | Zarling et al. ............... 435/7.92 |
| 6,847,443 | B1 |   | 1/2005  | Herod et al. |
| 7,058,267 | B2 |   | 6/2006  | Neuhaus et al. |
| 7,224,446 | B2 |   | 5/2007  | Kreh et al. |
| 7,248,354 | B2 |   | 7/2007  | Kreh et al. |
| 7,265,823 | B2 |   | 9/2007  | Kreh et al. |
| 7,292,328 | B2 |   | 11/2007 | Kreh et al. |
| 7,307,713 | B2 |   | 12/2007 | Kreh et al. |
| 7,327,450 | B2 |   | 2/2008  | Kreh et al. |
| 7,424,393 | B2 |   | 9/2008  | Halama et al. |

(Continued)

FOREIGN PATENT DOCUMENTS

DE   10 2004 029 014 A1   6/2004
DE   10 2005 061 834 B4   12/2005

(Continued)

*Primary Examiner* — Sath V Perungavoor
*Assistant Examiner* — Dakshesh Parikh
(74) *Attorney, Agent, or Firm* — Patentbar International, P.C.

(57) ABSTRACT

An apparatus (1) for the optical inspection of wafers is disclosed, which comprises an assembly unit (10) which carries optical elements (30, 31, 32, 33) of at least one illumination path (3) for a bright field illumination and optical elements (50, 51, 52, 60, 61, 62, 70, 71, 72, 80, 81, 82) of at least one illumination path (5, 6, 7, 8) for a dark field illumination. The assembly unit (10) furthermore carries plural optical elements (91, 92, 93, 94, 95, 96, 97, 98, 99, 100) of at least one detection path (9₁, 9₂). An imaging optical element (32) of the at least one illumination path (3) for the bright field illumination (30), imaging optical elements (51, 61, 71, 81) of the at least one illumination path for the dark field illumination, and imaging optical elements (91, 95, 96) of the at least one detection path (9) are designed in such a way that all illumination paths (3, 5, 6, 7, 8) and all detection paths (9₁, 9₂) are telecentric.

35 Claims, 20 Drawing Sheets

U.S. PATENT DOCUMENTS

| | | |
|---|---|---|
| 7,545,489 B2 | 6/2009 | Sulik et al. |
| 7,577,353 B2 | 8/2009 | Gaessler et al. |
| 7,602,481 B2 | 10/2009 | Kreh |
| 7,636,164 B2 | 12/2009 | Gaessler |
| 2003/0086083 A1 | 5/2003 | Ebert et al. |
| 2005/0219518 A1* | 10/2005 | Korngut et al. ............ 356/237.2 |
| 2005/0280808 A1 | 12/2005 | Backhauss |
| 2006/0146319 A1 | 7/2006 | Tsai et al. |
| 2006/0256326 A1* | 11/2006 | Bills et al. ................. 356/237.2 |
| 2008/0007726 A1 | 1/2008 | Fairley et al. |
| 2008/0144014 A1 | 6/2008 | Vollrath et al. |
| 2008/0144025 A1 | 6/2008 | Vollrath et al. |

FOREIGN PATENT DOCUMENTS

| | | |
|---|---|---|
| DE | 10 2007 022 831 B4 | 5/2007 |
| GB | 2332050 A | 6/1999 |
| JP | 2003017536 A | 1/2003 |
| JP | 2007183283 A | 7/2007 |

\* cited by examiner

APPARATUS FOR THE OPTICAL INSPECTION OF WAFERS

RELATED APPLICATIONS

This application claims priority to German Patent Application Nos. DE 10 2009 025 831.0 filed on May 19, 2009, and DE 10 2009 044 151.4 filed on Sep. 30, 2009, both of which are incorporated herein by reference in their entirety.

FIELD OF THE INVENTION

The present invention relates to an apparatus for the optical inspection of wafers.

BACKGROUND OF THE INVENTION

The German patent application DE 10 2006 059 190 A1 discloses an apparatus for the inspection of a wafer. For the inspection of the wafer at least one illumination system is provided, which emits a respective illumination light beam along a respective illumination path onto the surface of a wafer. A detection system defines a detection path, wherein the detection system exhibits a defined spectral sensitivity and collects data from at least one illuminated region on the surface of the wafer; the illuminated region is moving along a scan direction. The moving region can be evaluated within plural spectral ranges. The at least one illumination system is a continuous light source.

The German patent application DE 10 2007 002 711 A1 discloses an apparatus for the inspection of the surface of a wafer. The apparatus comprises at least one top-light illumination system for illuminating the surface of the wafer with a first and a second type of illumination. The first and the second type of illumination in particular are a bright field illumination and/or a dark field illumination. Furthermore an image capture device is provided to capture an image of the illuminated region. Moreover a system for storing intensity values is provided, in order to determine the colour of an optimized illumination of each type of top-light illumination.

The German patent DE 10 2004 029 014 B4 relates to a method and an apparatus for the inspection of a wafer. The method and the apparatus in particular are provided for the detection of macro defects, like for instance errors in exposure, wherein at least a part of the wafer surface is illuminated by a source of radiation. An image of this surface is recorded with a camera and is the basis for the inspection of the surface of the wafer. In order to conduct the detection of defects at optimal image contrast, it is proposed to illuminate the surface of the wafer telecentrically with a small illumination aperture. Therefore the source of radiation is provided with a corresponding system of lenses.

The German patent DE 10 2005 038 034 B3 shows an apparatus designed for bright field inspection with orthogonally incident light. The illumination system illuminates the surface of the wafer in the inspected area orthogonally from above with three narrow spectra, provided in the spectral ranges of red, green, and blue. The capture device captures the image formed by the light reflected from the inspected area orthogonally from above through the beam splitter. Due to the bright field inspection setup the light directed onto the inspected area by the illumination system interferes with transparent thin layers in the inspected area. Thus by interference effects fluctuations of layer thickness as well as of optical thickness can be reduced.

The US patent application US 2008/0007726 discloses an inspection system for wafers characterized by a high throughput. Light from a bright field illumination system is directed onto a review camera by a movable mirror. The dark field illumination system comprises a laser with an adjustable angle. The scattered light is detected with a TDI-sensor. The difference with the present invention is that the dark field illumination is done with a laser. For each type of illumination moreover a different detector is provided. There is no essentially identical capture of bright field images and dark field images of the surface of the wafer.

In the US patent application US 2006/0146319 an apparatus is disclosed for recording plural bright field images and plural dark field images from one and the same region on the surface of a wafer. In order to obtain information from the dark field illumination on the surface of the wafer, plural lasers are provided which differ in their frequencies. For the bright field illumination also plural light sources are provided, which also differ in frequency. For recording the different types of information, plural detectors are provided. The detectors receive the laser light scattered from the surface of the wafer through a spatial filter. The light from the bright field illumination system reaches the detector or detectors, respectively, which are TDI sensors, via a beam splitter. It is also possible to use a camera which is an RGB-camera provided with three CCD chips.

The Japanese patent application JP 2007-183283 shows two cameras, one camera being located in the bright field setup. With a second camera scattered light from the surface of the wafer can be recorded.

According to the Japanese patent application JP 2003-017536 two one-dimensional CCD cameras are disclosed, which record scattered light from two lasers. The light from the lasers impinges on the surface of the wafer with an angle. The intensity of the lasers can be monitored and controlled accordingly.

The German patent application DE 103 59 723 A1 discloses at least one microscopic top-light illumination system for directing a pulsed illumination beam onto a surface of a wafer and illuminating an area on the surface of the wafer. Furthermore an image capture device is provided in order to capture an image of the respective illuminated area of the surface of the wafer. Therein the illuminated area is smaller than the surface of the wafer. Furthermore a system is provided for detecting intensity fluctuations of the light pulses of the top-light illumination system and for controlling them accordingly.

In the German patent application DE 103 59 722 A1 defects on a wafer can be detected with bright field and or dark field illumination. The radiation incident on the wafer has a substantial effect on the reliability of the measurement results. In order to improve the reliability of the measurement results the wafer is illuminated with an illumination system wherein essentially its brightness and frequency are set with reference to previously stored nominal illumination values.

The German patent application DE 198 56 219 A1 discloses a fibre optical output coupling for monitoring the light intensity in a fibre optical cable. The outer covering layer is removed and the underlying cladding is roughened, so that light in the cladding is radiated out. A photodetector is positioned close to the polished surface and optically insulated from other light sources. The signal generated by the photodetector is an indication of the light intensity in the fibre. Control or adjustment, respectively, of the light intensity of the light sources is not discussed in this document.

The German patent application DE 103 52 590 A1 discloses a method for producing an optical fibre with an output coupling point for scattered light for monitoring the power of light passed through the optical fibre. The optical fibre comprises a core with a first refractive index, and a cladding surrounding the core with a second refractive index. The second refractive index is smaller than the first refractive index. A section of the optical fibre is essentially straight in the region of the output coupling point. The optical fibre is electrothermically treated at a location within the essentially straight section in such a way that in the boundary region of core and cladding a partial mixture of core material and cladding material is generated and thus scattering centres are produced, turning the treated location into the output coupling point.

The German patent application DE 103 30 003 relates to an apparatus for the inspection of a wafer. The apparatus comprises at least one illumination system for directing an illumination beam onto a surface of the wafer. An image capture device is provided for capturing an image of an illuminated area on the surface of the wafer in a plurality of spectral ranges. A colour changing device is provided for changing the colour of the illumination beam or of the reflected beam. The wafer inspection apparatus is characterised in that the colour changing device is designed in such a way that the colour spectrum of the illumination beam or of the image recorded from the surface of the wafer is adaptable to the spectral sensitivity of the image capture device.

U.S. Pat. No. 6,847,443 discloses a triple filter in the illumination path. In this way the wafer can be illuminated with three selectable wave lengths or wave length intervals, respectively. The disadvantage is that the light from the wafer reaches the camera provided for detection directly and without additional filtering.

The German patent application DE 103 30 506 A1 discloses an apparatus for the inspection of wafers. A table which is movable in two mutually orthogonal directions is supported on air bearings. The wafer to be inspected can be moved along a meander-like path with the table, in order to create a plurality of image windows, out of which the entire surface of the wafer can be composed.

The German patent application DE 103 51 848 A1 discloses a system for the detection of macro defects. The system is surrounded by a casing. The individual elements of the system are located in a first, a second, and a third section. The second section comprises a measurement table movable in X-coordinate direction and in Y-coordinate direction. Furthermore air guides are provided within the casing of the system, so that a flow of air can be produced over the wafer placed on the measurement table; the flow of air is essentially parallel to the wafer.

The German patent DE 103 30 005 B4 discloses an apparatus for the inspection of a wafer. The apparatus comprises at least one top light illumination system, which emits light into an illumination path, which encloses an angle with the surface of the wafer. Furthermore an image capture device is provided for recording an image of the surface in the dark field setup. Furthermore at least a dimmer is provided, which directs the light beam onto the surface of the wafer.

The German patent DE 103 30 006 B4 also discloses an apparatus for the inspection of a wafer. The apparatus comprises two light sources in a top light setup, which emit light onto the surface of the wafer in an optical path. The light from the light sources impinges onto the surface of the wafer under an angle. An image capture device records a corresponding image of the respectively illuminated image window. The two light sources are arranged in such a way that the illumination path of the light sources is orthogonal to the linear structures of the dies on the wafer.

The US patent application US 2003/0086083 A1 discloses a positioning system for a metrology apparatus. A beam splitter splits the light from the object to be measured into a first path and a second path. One path is provided for high magnification and the other path is provided for low magnification.

SUMMARY OF THE INVENTION

It is an object of the present invention to create an apparatus for the optical inspection of the surface of a wafer, providing a plurality of different recording options. Furthermore the apparatus is to be designed such that a high quality detection of the surface of the wafer is possible.

The above object is achieved by an apparatus for the inspection of wafers which comprises:

an assembly unit which carries optical elements of at least one illumination path for a bright field illumination and optical elements of at least one illumination path for a dark field illumination and the assembly unit carries several optical elements of at least a first detection path and a second detection path;

a plurality corresponding light sources provide the bright field illumination and/or the dark field illumination; an imaging optical element of the at least one illumination path for the bright field illumination; and a plurality of imaging optical elements of the at least one illumination path for the dark field illumination, and a plurality of imaging optical elements of the at least one first detection path and second detection path, wherein the imaging optical element of the at least one illumination path for the bright field illumination, the plurality of imaging optical elements of the at least one illumination path for the dark field illumination and the plurality of imaging optical elements of the at least one first detection path and second detection path are designed in such a way that all illumination paths and all detection paths are telecentric.

A further object of the present invention is to optimize the various types of illumination of the surface of the wafer so that an as high as possible percentage of the light emitted by the light sources reaches the surface of the wafer, in order to achieve an effective detection of the surface of the wafer.

The above object is achieved by an apparatus for the optical inspection of the surface of a wafer comprising:

an assembly unit, which carries a plurality of optical elements of an illumination path for a bright field illumination;

a plurality of optical elements of four illumination paths for a dark field illumination;

a plurality of optical elements of a first detection path and a second detection path;

a plurality of flash lights providing light for the bright field illumination and/or dark field illumination via corresponding optical fibres;

an imaging optical element of the at least one illumination path for the bright field illumination; optical elements of each of the four illumination paths for the dark field illumination and imaging optical elements of the first detection path and the second detection path are designed in such a way that all illumination paths for the bright field illumination and the dark field illumination and the first and second detection paths are telecentric;

a casing for the optical elements of the four illumination paths for the dark field illumination; and a several optical fibers which are configured to transport the light from the flash lights to each of the four illumination paths for dark field illumination via, wherein each optical fibre is connected with the casing by a fibre connector.

An additional object of the present invention is to create an apparatus for the optical inspection of the surface of a wafer which is of simple construction and easily accessible by service personnel at required service intervals. Here it is important to assure that the simplicity of construction does not adversely affect the quality of inspection of the surface of the wafer.

The above object is achieved by an apparatus comprising:

an assembly unit, which is located above a table which is movable in a X-coordinate direction and in a Y-coordinate direction and which carries the wafer wherein the assembly unit consists of a first board and a second board, wherein the first board exhibits an orientation essentially parallel to the surface of the wafer and the second board is connected orthogonally to the first board;

optical elements of an illumination path for a bright field illumination, optical elements of four illumination paths for a dark field illumination and plural optical elements of at least a first detection path are carried by the assembly unit;

a plurality of flash lights for providing light for the bright field illumination and/or dark field illumination wherein the light is provided via optical fibres; and an imaging optical element of the at least one illumination path for the bright field illumination, imaging optical elements of each of the four illumination paths for the dark field illumination, and imaging optical elements of the at least first detection path are designed in such a way that all illumination paths and the at least first detection path are telecentric.

For the inspection of the surface of the wafer an imaging optical element of the at least one illumination path for the bright field illumination is provided. Furthermore plural imaging optical elements of the at least one illumination path for the dark field illumination are provided. Also there are plural imaging optical elements in the detection path. The optical elements in the illumination path for the bright field illumination, the optical elements in the illumination path for the dark field illumination and the optical elements in the detection path are designed in such a way that all illumination paths and all detection paths are telecentric.

In the first detection path one of the optical elements is a first camera. The first camera is fitted with an objective as imaging optical element. In an embodiment the first camera can be a three-chip camera.

One of the optical elements in the illumination path is a mount with at least two different, changeable positions for filter elements. Thus the spectral composition of light in the illumination path is settable.

In the first detection path one of the optical elements is an output coupling means, which transmits part of the light in the first detection path into a second detection path. In the second detection path a second camera with an objective is provided as optical element. The objective is the imaging optical element. In an embodiment the second camera can be a high resolution monochrome camera.

It is obvious for a person skilled in the art that the first camera and the second camera can be of different type. The first and the second camera are chosen according to the respective measurement task of the user, so that a desired measurement result is achieved. Even though the subsequent description is restricted to a three-chip camera and/or a high resolution monochrome camera, this is not to be understood as a limitation of the invention.

In the first detection path furthermore a field lens is provided as imaging optical element. The field lens is located in the first detection path in front of the output coupling means.

In the first detection path an element is provided between the objective of the first camera and the field lens, wherein the element exhibits at least two different positions for filter elements. Likewise in the second detection path an element is provided between the objective and the second camera, wherein the element exhibits at least two different positions for filter elements.

The imaging optical elements of the at least one illumination path for the dark field illumination are set into a respective casing. Light is provided to each casing from light sources, which are flash lights. Light from the light sources is provided to the at least one illumination path for the dark field illumination through an optical fibre. The optical fibre is connected to the casing by a fibre connector.

To each casing there corresponds a tilted mirror as an optical element, which directs the dark field illumination onto the surface of the wafer under a correspondingly preset angle.

The optical elements for the bright field illumination and the optical elements for the dark field illumination are designed in such a way that a rectangular illuminated area is providable on the surface of the wafer, wherein the illumination of the illuminated area is homogeneous.

The assembly unit for the various optical elements is located above a table, movable in the X-coordinate direction and in the Y-coordinate direction, for the wafer. The assembly unit consists of a first board and a second board. The first board is essentially parallel to the surface of the wafer, which is placed on the table movable in the X-coordinate and in the Y-coordinate direction. The second board is connected with the first board essentially orthogonally.

The first board is connected with the second board by reinforcement elements. Parallel to the second board a further reinforcement element is provided, which divides the first board into a first section and a second section.

The first board essentially carries the plural optical elements for the at least one illumination path for the dark field illumination.

The first board exhibits a first mount position, a second mount position, a third mount position, and a fourth mount position. At the first mount position and at the second mount position, respectively, the casing for the optical elements is mounted. The resulting direction of propagation of light from the first mount position and from the second mount position encloses an angle of 45° with the X-coordinate direction of the dies arranged on the surface of the wafer. At the third mount position also a casing for the optical elements is mounted. Therein the mount position is arranged such that a direction of propagation of light from the third mount position is orthogonal to the X-coordinate direction of the dies arranged on the surface of the wafer. At the fourth mount position also a casing for the optical elements is mounted. The casing at the fourth mount position is arranged in such a way that a direction of propagation of light from the fourth mount position is parallel to the X-coordinate direction of the dies arranged on the surface of the wafer.

A tilted mirror is arranged on the casing in such a way that a central ray of light from the first mount position and the second mount position of the dark field illumination impinges on the surface of the wafer under an angle in the interval from 3° to 10°.

Furthermore a tilted mirror is arranged on the casing in such a way that a central ray of light from the third mount position and the fourth mount position of the dark field illumination impinges on the surface of the wafer under an angle in the interval from 15° to 25°.

The casing for the optical elements at the third mount position is exchangeable for the casing of the optical elements, wherein the tilted mirror is arranged in such a way that a central ray of light from the third mount position impinges on the surface of the wafer under an angle in the interval from 20° to 40°.

Furthermore a fifth mount position is provided on the first board for a reading device. The reading device is provided for evaluating an identification mark on the wafer.

Furthermore the first board exhibits a sixth mount position for a device provided for the geometrical alignment of the wafer. The device can furthermore be used for assessing the edge bead removal at the edge of the wafer.

The second board essentially carries the plural optical elements of the at least one detection path. Likewise the second board carries the plural optical elements of the at least one illumination path for the bright field illumination of the surface of the wafer.

The second board carries the first camera. Furthermore the second board exhibits a mount position for an optional second camera. The imaging optical element of the at least one illumination path for the bright field illumination is also carried by the second board. The field lens is carried by the second board in such a way that it is part both of the first and the second detection path. Furthermore the second board carries plural elements, which exhibit at least two different, changeable positions for filter elements. The second board also carries a casing for the elements for the bright field illumination.

A detection system is provided in order to determine the amount of light from the light sources, which are flash lights, and also in order to make adjustments if necessary. The light from the flash lights is guided through a respective optical fibre. Each optical fibre exhibits a coupling-out interface, where part of the light of the respective flash light is transmittable to the detection system.

According to a preferred embodiment the coupling-out interface is connected to a further optical fibre, which exhibits a fibre connector at its free end. By the fibre connector the light coupled out is transmittable to the detection system.

The light exiting the fibre connector is transmittable to three different diodes by two dichroic beam splitters. These diodes form the detection system by which the intensity of the individual spectral components of the light in the optical fibre, or the light from the flash lights, respectively, is measureable. Several embodiments of the detection system are possible. For example, the detection system can be a three-quadrant diode. A further possibility is to direct, or image, respectively, the light exiting the fibre connector on a surface detector. The apparatus for the optical inspection of wafers achieving one of the above objects can be designed in such a way that the apparatus comprises an assembly unit carrying optical elements of an illumination path for a bright field illumination and optical elements of four illumination paths for a dark field illumination. The assembly unit carries plural optical elements for a detection path. The light for the bright field and/or dark field illumination originates from corresponding flash lights, wherein the light from the flash lights is guided through optical fibres. An imaging optical element of the at least one illumination path for the bright field illumination, the imaging optical elements of each of the four illumination paths for the dark field illumination and the imaging optical elements of the at least one detection path are designed in such a way that all illumination paths and the detection path are telecentric. The optical elements of the four illumination paths are located in respective casings. The light from the flash lights is provided to each of the four illumination paths for the dark field illumination through an optical fibre, wherein the optical fibre is connected with the casing by a fibre connector.

At least one of the abovementioned objects of the invention is achieved by an apparatus for the optical inspection of wafers wherein the apparatus comprises an assembly unit located above a table movable in X-coordinate direction and in Y-coordinate direction. The movable table carries the wafer to be inspected. The assembly unit carries optical elements of an illumination path for a bright field illumination and optical elements of four illumination paths for a dark field illumination. Likewise the assembly unit carries plural optical elements for a detection path. The light for the bright field illumination and/or the dark field illumination is provided by corresponding flash lights through optical fibres. An imaging optical element of the at least one illumination path for the bright field illumination, an imaging optical element of each of the four illumination paths for the dark field illumination, and the imaging optical elements of the detection path are designed in such a way that all illumination paths and the detection path are telecentric. The assembly unit consists of a first board and a second board. The first board is essentially parallel to the surface of the wafer and the second board is connected orthogonally with the first board.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
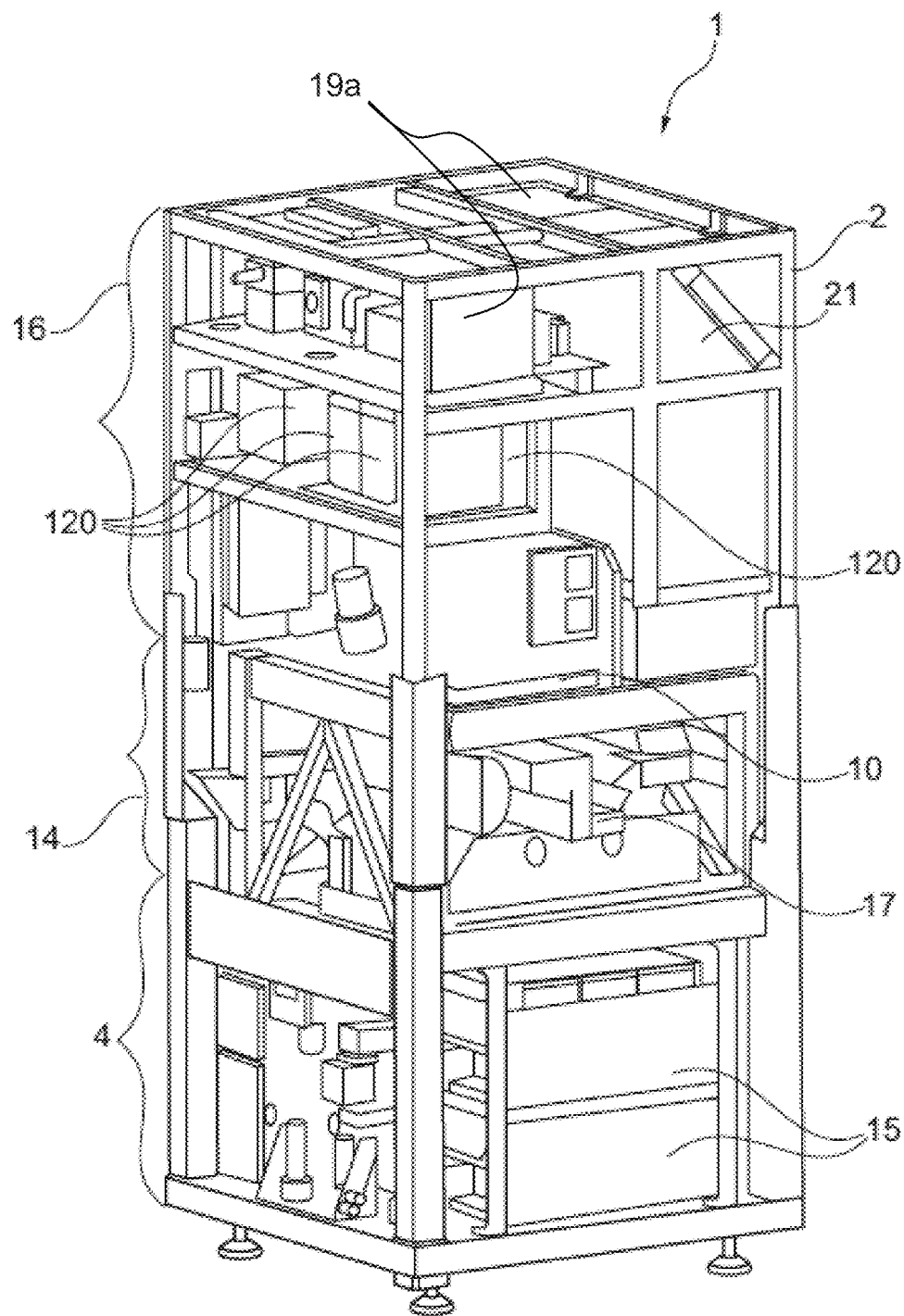
FIG. 1 shows a perspective view of the basic module of the apparatus for the inspection of wafers.

Identical reference numerals are used for like elements of the invention or elements of like function. Furthermore only those reference numerals are shown in the individual figures which are required for the description of the respective figure.

FIG. 1 shows a perspective view of an apparatus 1 for the optical inspection of a wafer. The apparatus 1 comprises a frame 2, within which a plurality of elements, required for the inspection, are mounted. The apparatus 1 essentially consists of a first section 4, a second section 14, and a third section 16. The apparatus 1 can be completely closed with walls (not shown) at the outside surfaces. Therein the walls are attached to the frame 2 of the apparatus 1. In the interior of the frame 2 a defined climate or clean-room conditions, respectively, can be set. The first section 4 of the apparatus 1 comprises plural control units, or control computers 15, respectively, which cooperate in the capture and evaluation of images of the surface of the wafer. Likewise the control units, or control computers 15, respectively, are responsible for the control of the individual components of the apparatus 1.

In the second section 14, which is located between the first section 4 and the third section 16, a table 17 movable in the X-coordinate direction and in the Y-coordinate direction is provided. The wafer to be inspected is placeable on the table 17 movable in the X-coordinate and the Y-coordinate direction. Placement of the wafer on the table 17 movable in X-coordinate direction and in Y-coordinate direction is done by adequate robotic systems (not shown), which are well established in the state of the art.

In the third section 16 an assembly unit 10 is provided, which is located immediately next to the second section 14 of the apparatus 1. The assembly unit 10 carries a plurality of optical elements for illumination, imaging, and detection, respectively, which will be discussed in more detail in the subsequent description. Furthermore a plurality of light sources 120 is provided in the third section 16, wherein the light sources are flash lights. Likewise the control electronics 19a required for the light sources 120 is mounted within the third section 16. Light from the light sources 120 is guided to the optical elements on the assembly unit 10 by respective optical fibres (not shown here). Furthermore an intake 21 for air is provided in the third section 16, wherein the air is guided within the apparatus 1 by adequate means along correspondingly provided and selected directions.

Figure 2:
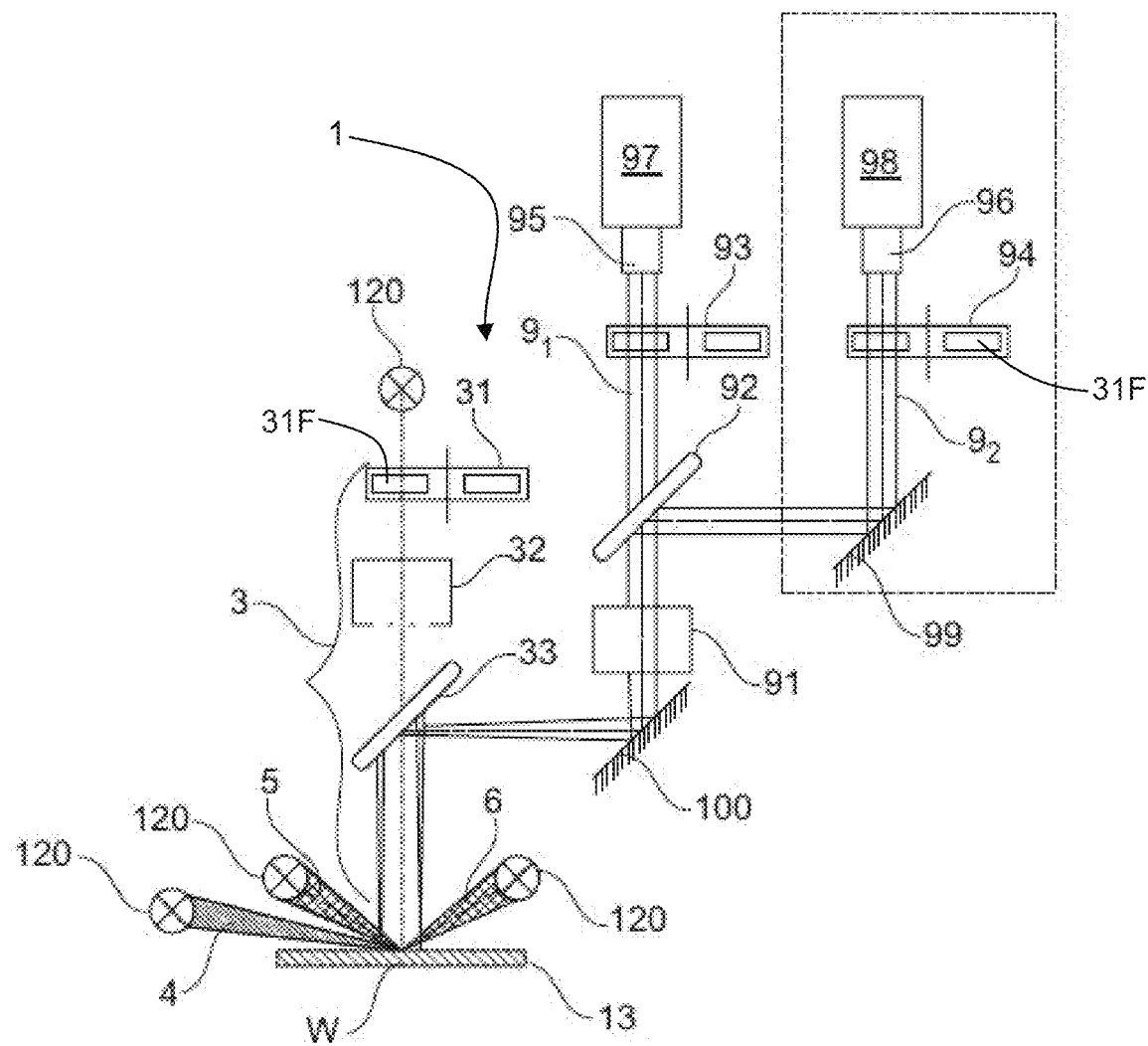
FIG. 2 shows the schematic layout of the apparatus for the optical inspection of wafers according to the invention.

FIG. 2 schematically shows the layout of the apparatus 1 for the inspection of the surface 13 of a wafer W. The elements shown in FIG. 2 are essentially provided on the assembly unit 10 (see FIG. 1). At least one illumination path 3 is provided for the bright field illumination. Plural optical elements 31, 32, 33 are provided in the illumination path 3. Thus there is provided in the illumination path 3 for the bright field illumination an optical unit 30, which transmits the light from the corresponding flash light into the illumination path 3 for the bright field illumination. Likewise, an imaging optical element 32 is provided in the illumination path 3 for the bright field illumination, wherein the imaging optical element 32 is designed in such a way that it provides for a telecentric illumination of a certain illuminated area (not shown here) on the surface 13 of the wafer W. A further optical element 31, which carries plural filter elements $31_F$, is provided in the illumination path 3 of the apparatus 1. The further optical element 31 may be designed as a slider or a filter wheel. Furthermore the illumination path 3 for the bright field illumination comprises an optical element 33, which is a dichroic beam splitter. The dichroic beam splitter 33 directs the light reflected from the surface 13 of the wafer W into the first detection path $9_1$ and into the second detection path $9_2$. Moreover plural further light sources 120 are provided for the surface 13 of the wafer W, which, together with additional optical elements (not shown here), provide for a corresponding dark field illumination of the surface 13 of the wafer W.

The first detection path $9_1$ is provided with a first camera 97. Light reflected from the surface 13 of the wafer W first reaches a tilted mirror 100 from the dichroic beam splitter 33 in the illumination path 3 for the bright field illumination. The light is directed into the first detection path $9_1$ by the tilted mirror 100. Plural optical elements 91, 92, 93 and 95 are provided in the first detection path $9_1$, which are designed in such a way that telecentric imaging onto the detector of the first camera 97 occurs.

A spectrally sensitive output coupling means 92 is also provided in the first detection path $9_1$ as an optical element which directs light into the second detection path $9_2$. Light thus is directed into the first detection path $9_1$ or into the second detection path $9_2$ according to a desired spectral composition. The light in the second detection path $9_2$ reaches the second camera 98 from a tilted mirror 99. In the second detection path $9_2$, also, optical elements 91, 92, 94, 96 and 98 are provided, which are designed in such a way that telecentric imaging occurs onto the second camera 98, too. The imaging optical elements 95 and 96 in the first detection path $9_1$ and in the second detection path $9_2$ are designed in such a way that a single field lens 91 is part of both the first detection path $9_1$ and the second detection path $9_2$. The single field lens 91 is responsible for both the imaging by the objective 95 of the first camera 97 and for the imaging by the objective 96 of the second camera 98. In FIG. 2 the section holding the second camera 98 is marked by a dotted border. This is to indicate that the second camera 98 is optional. However, the basic setup of the apparatus 1 for the inspection of the surface 13 of a wafer W already contains the spectrally sensitive output coupling means 92, which can be a beam splitter, in the first detection path $9_1$ of the apparatus 1, in order to facilitate as much as possible the addition of a second camera 98. In order to add a second camera 98 and the optical elements thus required, only the elements of the second detection path $9_2$ need to be attached to the respective mount positions provided on the assembly unit 10 (not shown).

Figure 3:
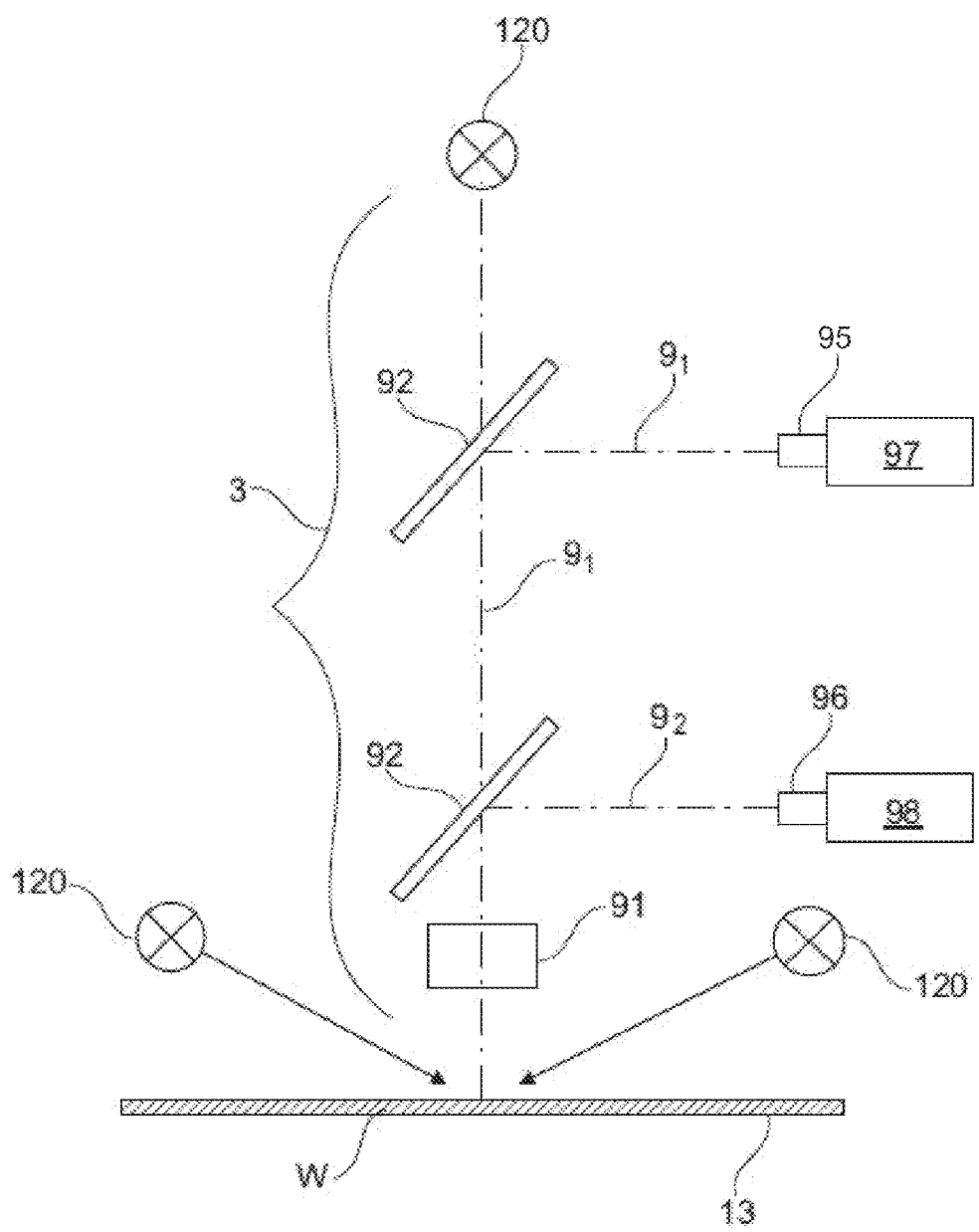
FIG. 3 shows a further embodiment of the apparatus for the optical inspection of wafers, wherein two cameras are employed.

FIG. 3 schematically shows the layout of a further embodiment of the apparatus 1 according to the invention for the optical inspection of the surface 13 of a wafer W. For recording an image of the surface 13 of a wafer W a first camera 97 and a second camera 98 are provided. One of the cameras 97, 98 is located in the bright field setup for capturing images. The other of the two cameras 97, 98 is located in the dark field setup. At least one illumination system 30 (see FIG. 11) for the bright field illumination is provided. Furthermore plural illumination systems 50, 60 (see FIG. 11) for the dark field illumination are provided. The apparatus 1 comprises a first detection path $9_1$ and a second detection path $9_2$. The first camera 97 with the corresponding telecentric objective 95 for the bright field illumination is located in the first detection path $9_1$. The second camera 98 with the corresponding telecentric objective 96 for monochrome high resolution imaging is located in the second detection path $9_2$. The illumination path 3 for the bright field illumination runs along the first detection path $9_1$. The detection paths $9_1$ and $9_2$ are coupled out of the illumination path 3 by beam splitter 92. Immediately above the surface 13 of the wafer W the field lens 91 is provided. The field lens 91 thus is part of both the objective 95 of the first camera 97 and the objective 96 of the second camera 98. In the proposed setup the first camera 97 is located in such a way that light, which eventually reaches the first camera 97, has been diminished in intensity by four passes through the two beam splitters 92. Since the intensity of the light source 120 for the bright field illumination required to achieve good contrast is usually easily accomplished technically, only small disadvantages in the bright field are incurred by this setup. The dark field illumination is independent of the arrangement of the beam splitters 92 in the illumination path 3. In the dark field, achieving sufficient intensity for recognizing image content is much more difficult than in the bright field. Therefore it is an advantage of this setup that for dark field image capture, which is done with the second camera 98, only one beam splitting step is necessary. Put differently, directing the light into the second detection path $9_2$ and onto the second camera 98 involves only a single redirection by a beam splitter 92. Possible polarisation effects in the bright field can be reduced by rotating the beam splitters 92 and/or one of the cameras 97, 98 by 90° with respect to each other about the illumination axis of the illumination path 3 for the bright field illumination.

Figure 4:
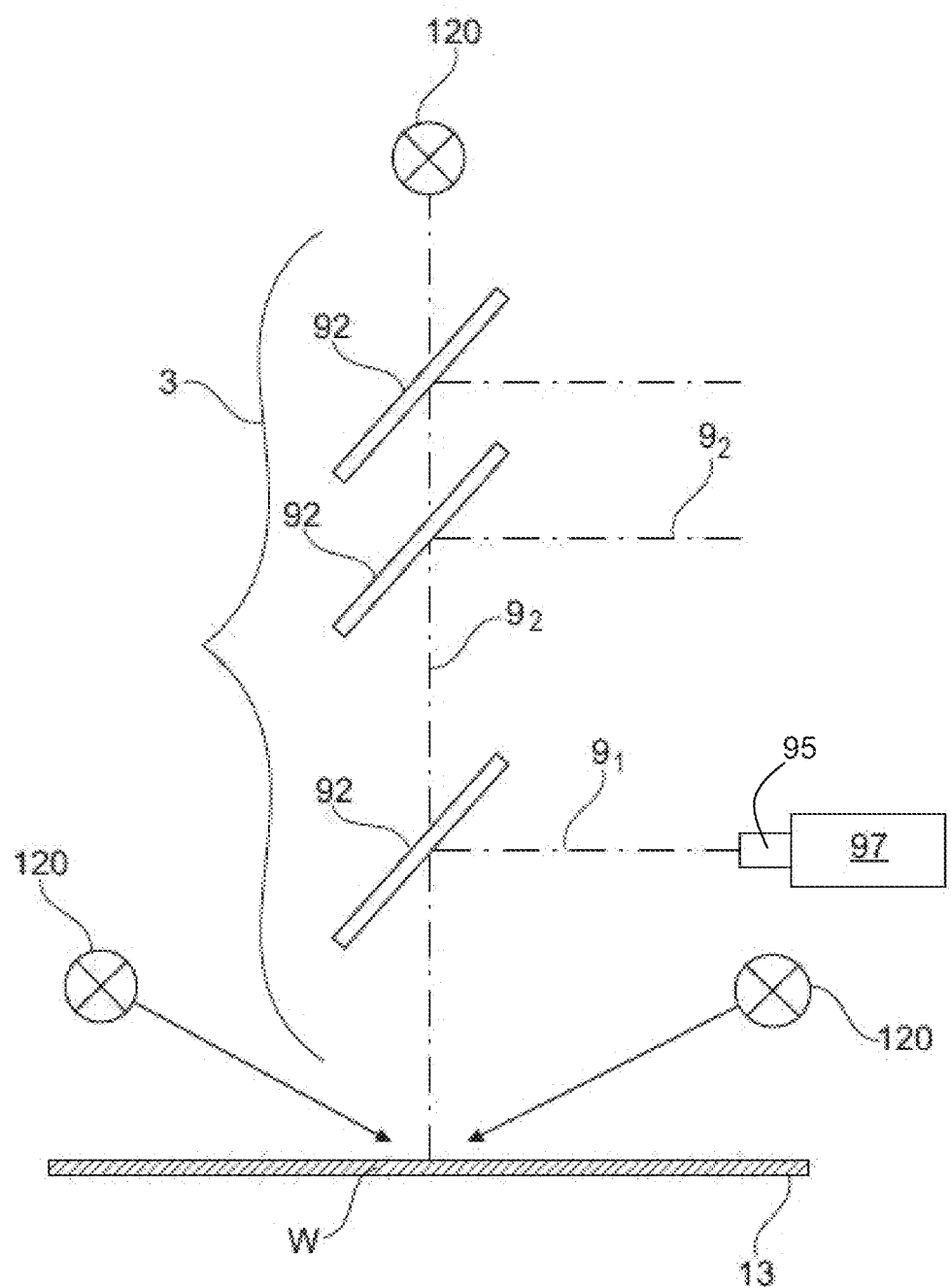
FIG. 4 shows an additional embodiment of the optical inspection of the surface of wafers.

FIG. 4 shows a further schematic layout of an embodiment of the arrangement of the optical elements in the apparatus 1 for the inspection of the surface 13 of a wafer W. In this embodiment, too, the illumination path 3 runs along the at least one detection path $9_1$. In the representation shown only the first camera 97 with the corresponding objective 95 is shown. Again a field lens 91 is provided above the surface 13 of the wafer W. Two beam splitters 92 are provided as so-called "dummy beam splitters" in the illumination path 3 of the light source 120 for the bright field illumination in addition to the beam splitter 92 which directs the light onto the first camera 97. As only a single camera 97 is provided in this embodiment, simultaneous image capture for both bright field illumination and dark field illumination is done with this camera 97. The dark field illumination is provided by plural light sources 50, 60. The additional beam splitters 92 in the illumination path 3 for the bright field illumination lead to approximately equal conditions of light for the bright field illumination and the dark field illumination at the camera 97. The light from the light source 120 for the bright field illumination needs to be suitably dimmed so that its intensity is adjusted to the intensity of the light which reaches the camera 97 from the dark field illuminations 50, 60. With this setup approximately the same intensities are achieved in the bright field as in the separate, time-shifted case, as the same number of passes through the beam splitters occurs. The dark field is unaffected, as already mentioned in FIG. 3. Possible polarisation effects in the bright field can be reduced by rotating the beam splitters by 90° with respect to each other about the axis of the illumination path 3.

The embodiments of the apparatus 1 for the inspection of the surface 13 of a wafer W described in FIGS. 3 and 4 also can be used advantageously if spectral aspects matter or splitting ratios different from 50:50 are used. In the case of embodiments with a first camera 97 and a second camera 98 combinations of bright field and dark field image capture in one of the two cameras 97, 98 is conceivable. Also, the top one of the two cameras can capture from the dark field, too. The corresponding matching to a single-camera setup is, however, always limited to the images captured by the first, or bottom, respectively, camera in the apparatus.

Figures 5, 6:
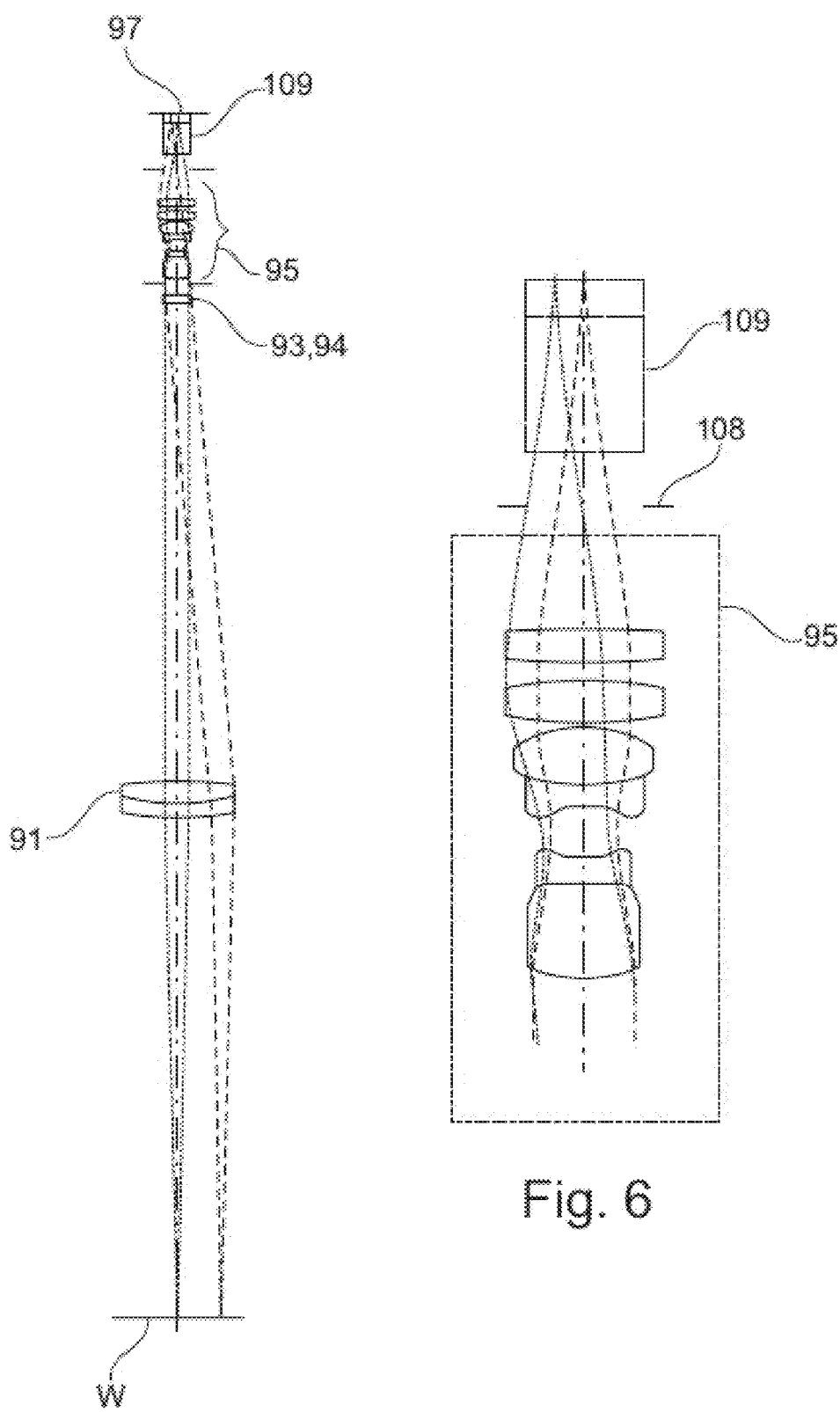
FIG. 5 shows the light path in the detection path and the optical elements of the detection path for telecentric imaging.
FIG. 6 shows a magnified view of the camera lens.

FIG. 5 schematically shows the arrangement of the optical elements 91, 93 and 95 in the detection path $9_1$ of the first camera 97. As already mentioned in the description of FIG. 2, the field lens 91 is part both of the first detection path $9_1$ and of the second detection path $9_2$. In this embodiment the first camera 97 is a three-chip CCD camera. A prism 109 is provided to spectrally distribute the light reflected from the surface of the wafer W to the individual chips of the camera 97. For the first camera 97 there is provided an objective 95, which cooperates with the field lens 91 in order to achieve double telecentric imaging. A position for an optical element 93, 94 which carries at least one filter is provided before the objective 95. The optical element 93, 94 can be a filter slider or a filter wheel.

FIG. 6 shows a detailed view of the objective 95 of FIG. 5. The light reflected from the surface of the wafer W is imaged onto the chips of the camera by the objective 95. Behind the objective 95 the light passes a stop 108 and is spectrally and spatially split between the individual chips (not shown) of the camera by the prism 109. During manufacture the objective 95 of the camera is adapted to the spatial position of the individual chips in the camera in such a way that an optimum imaging onto the chips of the camera is achievable.

Figures 7, 8:
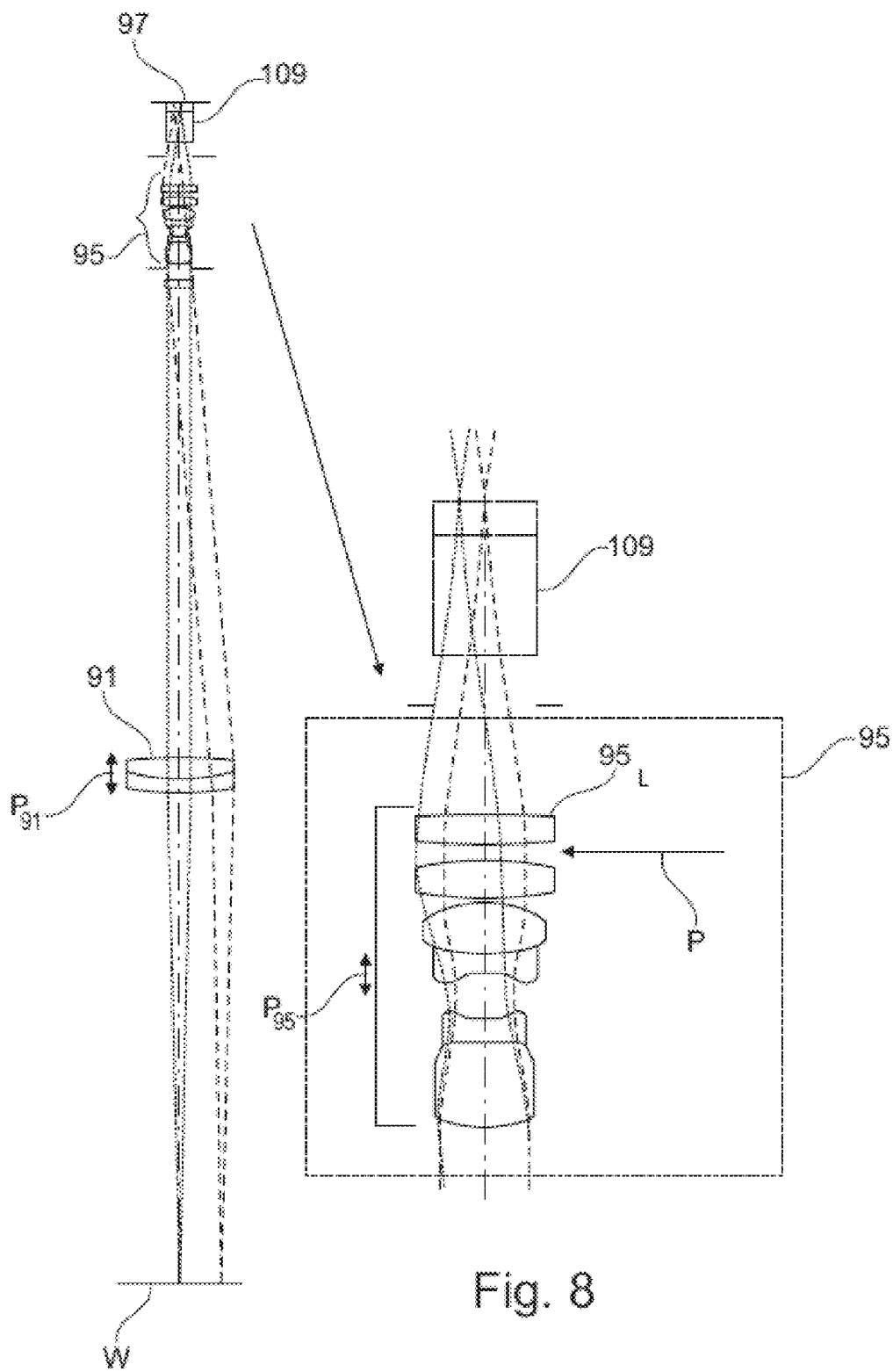
FIG. 7 shows the possibility of adjusting the field lens in the detection path.
FIG. 8 shows a detailed view of the camera lens and the possibility of setting the various elements of the camera lens.

FIG. 7 again shows the arrangement of the optical elements 91, 95 and 97 in the first illumination path $9_1$ of the apparatus 1 according to the invention for the inspection of the surface of a wafer W. In combination with FIG. 8 it is shown how the optically imaging elements 91 and 95 in the first detection path $9_1$ are alterable or adaptable, respectively, in order to achieve optimum imaging of the surface of the wafer W onto the chip or the chips of the camera 97. An adaption of focus of both the first detection path $9_1$ and the second detection path $9_2$ is achievable by displacing the field lens 91 along the double arrow $P_{91}$, as shown in FIG. 7. In FIG. 8 the change of the focus position is shown. The focus position of the objective 95 is achieved by changing the length of the objective 95 along the double arrow $P_{95}$ in FIG. 8. The adjustment of the focus position is achieved by changing at least the distance of the lens $95_L$, which is immediately opposite the camera 97 or the stop, respectively. The change of the distance is represented in FIG. 8 by the arrow P. The objective 95 for the camera is shipped calibrated and with the distances between the individual lenses fixed.

Figure 9:
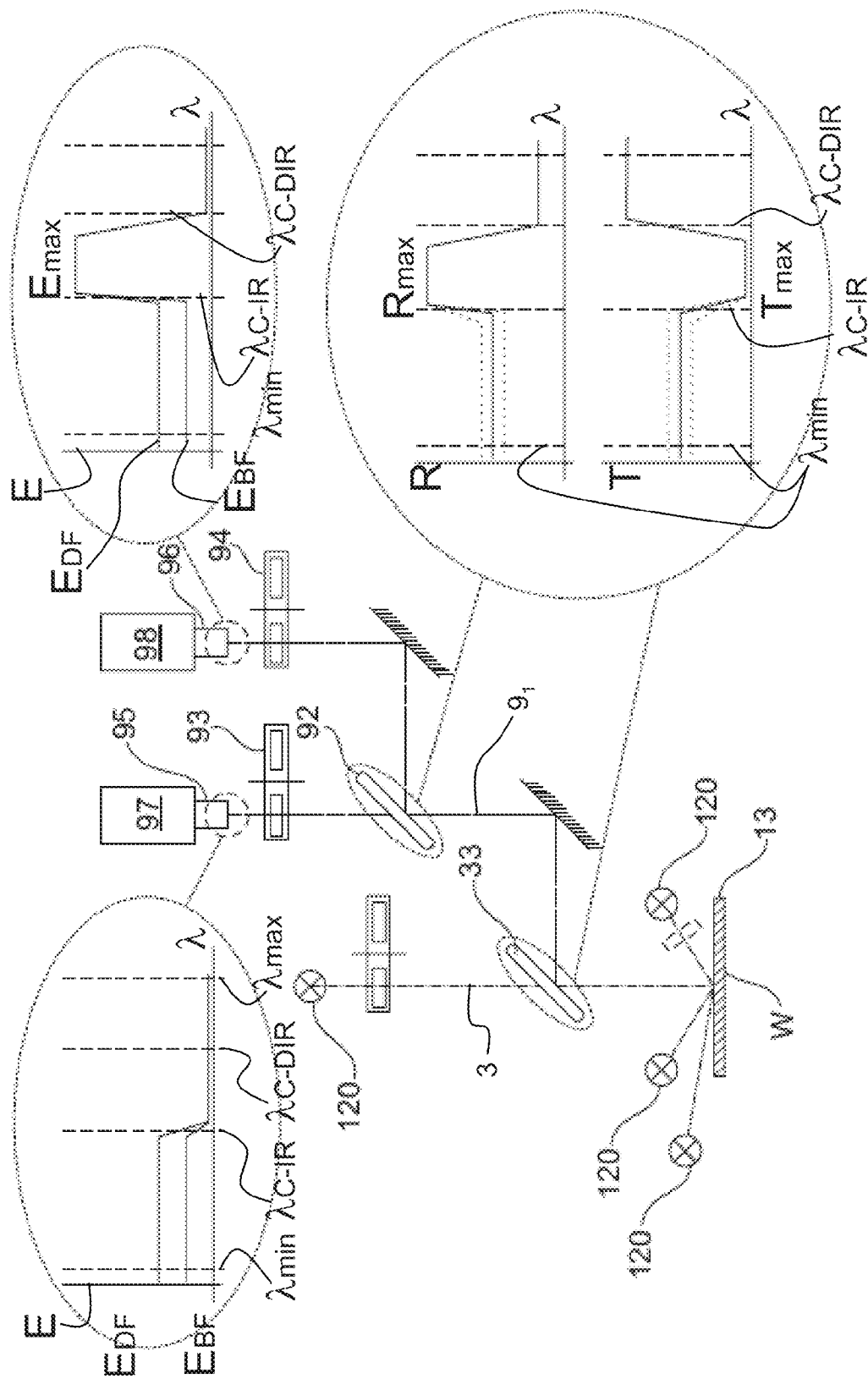
FIG. 9 shows a schematic view of the layout of the apparatus for the inspection of the surface of a wafer and of the spectral properties of the beam splitters.

FIG. 9 illustrates the optical properties of the beam splitters 33 in the illumination path 3 and of the beam splitter 92 in the first detection path $9_1$. The spectral characteristic of the objective 95 of the first camera 97 is such that it is transmissive up to a wave length $\lambda_{C\text{-}IR}$. Thus the objective 95 of the first camera is essentially transparent for visible light. In contrast, the objective 96 of the second camera exhibits a transmissivity in the visual range which corresponds to the transmissivity of the objective 95 of the first camera. Starting at $\lambda_{C\text{-}IR}$ the transmissivity increases until reaching a maximum $E_{max}$. At a wave length $\lambda_{C\text{-}DIR}$ the transmissivity then drops almost to zero. The transmission and reflection characteristics of the beam splitter 33 in the illumination path 3 and of the beam splitter 92 in the first detection path $9_1$ are such that both beam splitters 33 and 92 are 50/50 beam splitters. Thus their transmission characteristic is such that 50% of incident light is allowed through. Therein the beam splitter 33, or 92, respectively, is such that from a certain wave length $\lambda_{C\text{-}IR}$ on the transmissivity drops to zero. At a wavelength $\lambda_{C\text{-}DIR}$ the transmissivity of the beam splitter reaches a value above 50%. The reflection characteristics of the beam splitters 33 and 92 show similar behaviour. Thus about 50% of the light in the visual range is reflected. At a wavelength $\lambda_{C\text{-}IR}$ the reflectivity reaches a maximum value $R_{max}$. This implies that a large portion of the light in the infrared spectral range is reflected. The reflectivity drops to a value somewhat above zero at a wavelength $\lambda_{C\text{-}DIR}$. The reflectivity then is less than or equal to roughly 10%.

Figure 10:
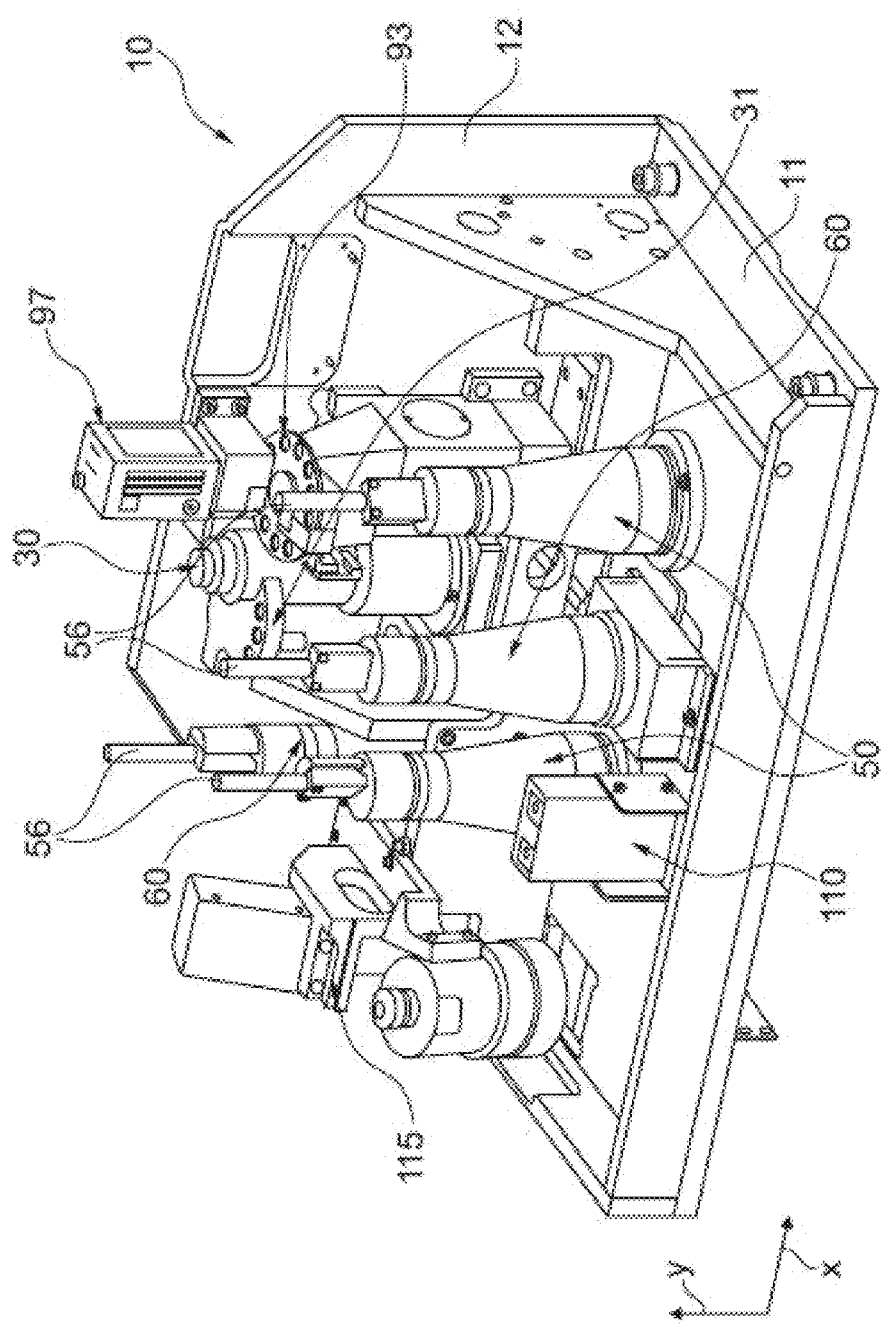
FIG. 10 shows a perspective view of the assembly unit as it is used in the invention and its elements, which are located on the assembly unit.

FIG. 10 is a perspective view of the assembly unit 10 carrying the plurality of optical elements required for the illumination and/or imaging of the surface of the wafer. The assembly unit 10 consists of a first board 11 and a second board 12. The first board 11 is arranged within the apparatus 1 in such a way that it is essentially parallel to the surface 13 of the wafer W. The first board 11 is orthogonally connected with the second board 12. The first board 11 of the assembly unit 10 carries the optical elements 50, 60, 70, and 80 for the dark field illumination. Two optical elements 50 are provided on the first board 11 which illuminate the dies on the surface 13 of the wafer W under an angle of 45° with respect to the X-coordinate direction. Furthermore an optical element 60 is provided on the first board 11, which directs light with a direction of propagation orthogonal to the X-coordinate direction onto the surface 13 of the wafer W. Additionally on the first board 11 an optical element 70 directs light with a direction of propagation parallel to the X-coordinate direction onto the surface 13 of the wafer W. The apparatus according to the invention is suitable for the inspection of both blank and structured wafers. In the case of structured wafers W light parallel to the dies D arranged in X-coordinate direction on the surface 13 of the wafer W is provided.

Furthermore a reading device 110 for evaluating an identification mark on the wafer W is provided on the first board 11. A further optical device 115 is also provided on the first board. The optical device 115 serves for the geometric alignment of the wafer W and also for determining the edge-bead removal (EBR) of the wafer edge $W_R$. Usually the wafer edge can be inspected with respect to the different criteria with this setup.

The second board 12 of the assembly unit 10 essentially carries the optical elements 91, 92, 93, 94, 95, 96, 97, 98, 99, and 100 for the at least one detection path $9_1$, or $9_2$, respectively. Also, the second board 12 carries the optical elements 30, 31, 32, 33 for the at least one illumination path 3 for the bright field illumination. In the representation of FIG. 10 only the first camera 97 is attached to the second board 12 of the assembly unit 10. The second board 12 exhibits a recess $12_2$ for the second camera 98, which therefore can easily be mounted at this recess $12_2$, if necessary. By this recess $12_2$ already a precalibration of the second camera 98 in the second detection path $9_2$ is provided. The following description therefore is restricted to the optical elements in the first detection path $9_1$. Apart from the first camera 97 a filter wheel 93 is provided on the second board 12. Likewise the beam splitter 92 is attached to the second board 12, which ultimately is responsible for coupling out the second detection path $9_2$. The casing for the beam splitter 92 is a board which only needs to be removed if a second camera 98 is used, so that the light can enter the second detection path $9_2$ from the casing $92_G$. In addition the second board carries the optical elements 30, 31, 32, and 33 of the illumination path 3 for the bright field illumination. Light for the dark field illumination and for the bright field illumination is provided via corresponding optical fibres 56. For the bright field illumination 30 a filter wheel 31, which allows to insert corresponding filters into the illumination path, is provided immediately behind the fibre connector. The corresponding beam splitter 33 of the illumination path 3 is also attached to the second board 12.

Figure 11:
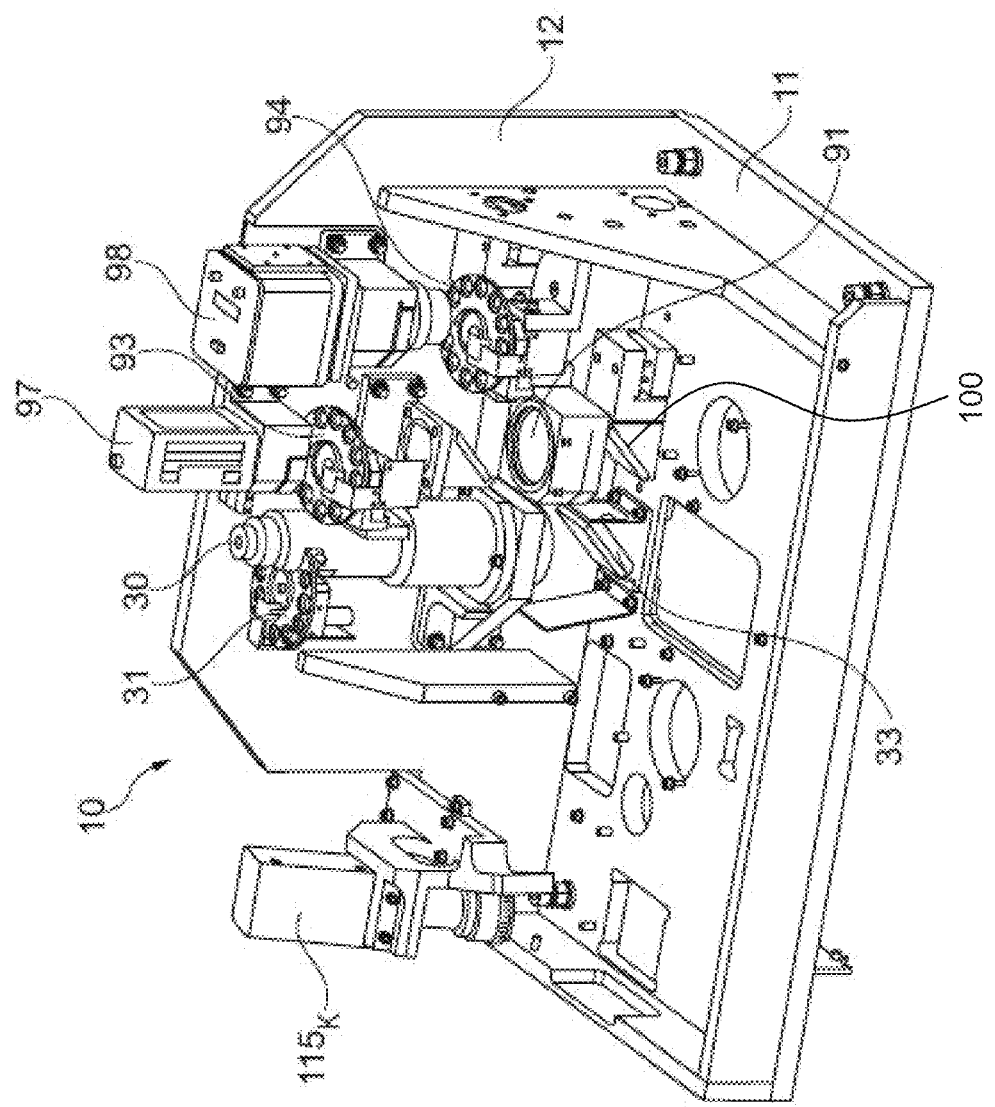
FIG. 11 shows a perspective view of the assembly unit, wherein some parts have been removed in order to achieve a clearer representation of the layout of the assembly unit and of the individual elements.

FIG. 11 is a further perspective representation of the assembly unit 10 with some elements removed, in order to afford a better view of the arrangement of the optical elements on the second board 12 of the assembly unit 10. As already mentioned in the description of FIG. 10, the second board 12 of the assembly unit 10 at least carries the optical unit 30 for the illumination in the illumination path 3 for the bright field illumination. The illumination 30 for the bright field illumination is enclosed by a casing so that no scattered light from the bright field illumination reaches other elements of the apparatus 1, which would adversely affect the results of measurements. An element 31 carrying plural filters engages the casing $30_M$ of the illumination 30 for the bright field illumination. In the embodiment shown the element 31 is a filter wheel. The first board 11 carries the beam splitter 33 for the bright field illumination. The beam splitter 33 directs the light reflected from the surface 13 of the wafer W onto a corresponding tilted mirror 100 which is also located on the first board 11 of the assembly unit 10. From the tilted mirror 100 the light first reaches the field lens 91, which is carried by the second board 12. From there it reaches the beam splitter 91, which splits the light into the first detection path 9₁ and the second detection path 9₂. The beam splitter 92 is also carried on the first board 11. In the embodiment shown the second camera 98 is also mounted on the second board 12. The second camera 98 carries the objective 96. The second board 12 also carries a mount point for a camera 115$_K$ for determining the geometrical alignment of the wafer and for determining the edge-bead removal of the wafer edge or for the general inspection of the wafer edge.

Figure 12:
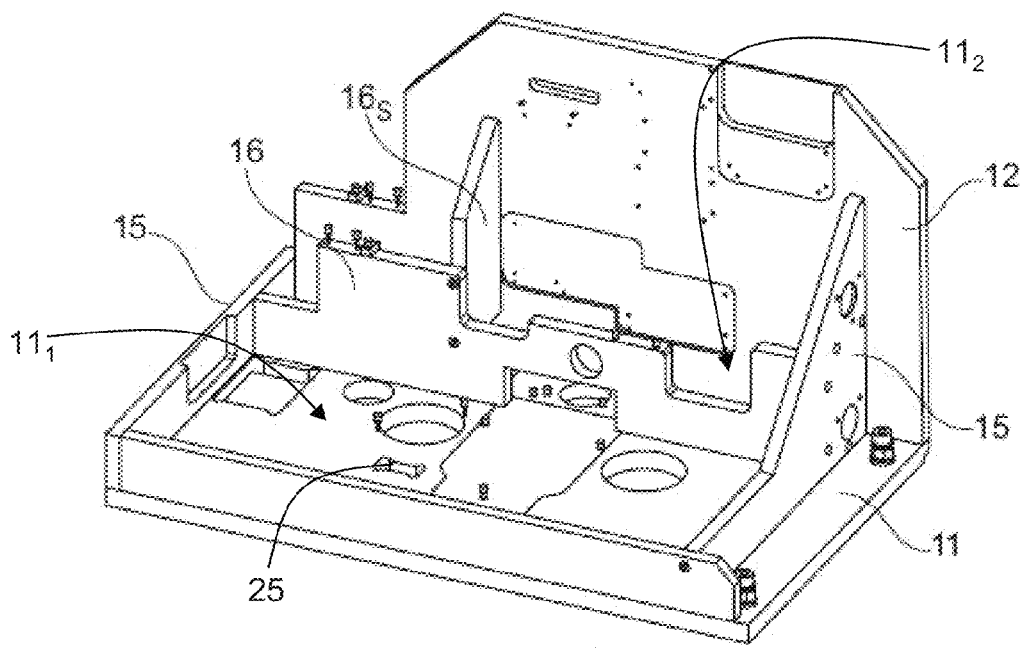
FIG. 12 shows a perspective view of the assembly unit carrying no elements.

FIG. 12 shows a perspective view of the assembly unit 10 with all optical elements removed, in order to reveal the design of the assembly unit 10. The assembly unit 10, as has already been mentioned, consists of a first board 11 and a second board 12. The first board 11 and the second board 12 are orthogonal to each other. The first board 11 is connected with the second board 12 by two reinforcement elements 15 located sideways. A further reinforcement element 16 is parallel to the second board 12. This further reinforcement element 16 divides the first board 11 into a first section 11₁ and a second section 11₂. As has already been mentioned, the layout of the assembly unit 10 is such that the first board 11 essentially carries the optical elements for the dark field illumination. The second board 12 essentially carries the optical elements of the illumination path for the bright field illumination and the optical elements responsible for the imaging of the surface 13 of the wafer W and for detecting the light from the surface 13 of the wafer W. This separation is particularly advantageous, because at possible service intervals easy and orderly access to the individual elements of the apparatus 1 for the inspection of the surface 13 of the wafer W is possible. In addition exchange and retrofitting of the apparatus is greatly facilitated, as the individual optical elements, which are provided for the inspection of the surface of the wafer with different illumination types (dark field or bright field illumination) are arranged on the first board 11 or on the second board 12 of the assembly unit 10.

Figure 13:
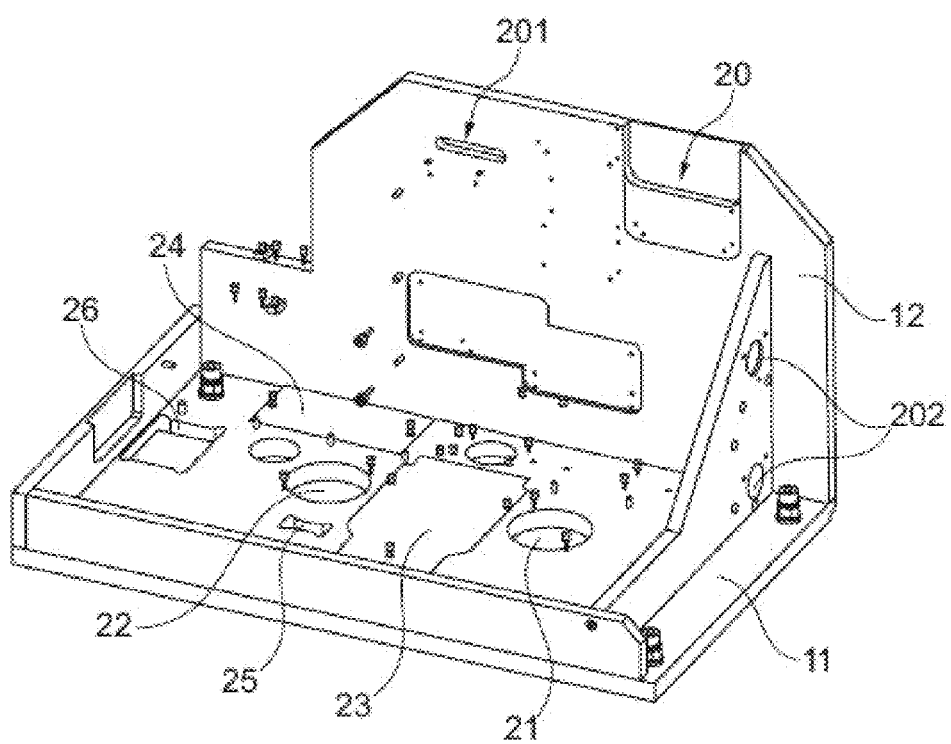
FIG. 13 shows a further perspective view of the assembly unit with the reinforcement elements removed.

FIG. 13 also is a perspective view of the assembly unit 10 with the reinforcement element 16 which is oriented parallel to the second board 12 and the corresponding support element 16$_{SD}$ removed. FIG. 13 clearly shows the various mount positions provided on the first board 11 or on the second board 12. The first board 11 exhibits a first mount position 21 and a second mount position 22 for mounting the optical elements of the dark field illumination so that a direction of propagation of light from the first mount position 21 and from the second mount position 22 include an angle of 45° with the X-coordinate direction of the dies D (see FIG. 22) arranged on the surface of the wafer. On the third mount position 23 optical elements can be mounted which emit light for the dark field illumination in a direction of 90° with respect to the X-coordinate direction. On the fourth mount position 24 optical elements can be mounted, which emit light for the dark field illumination parallel to the X-coordinate direction. On a fifth mount position 25 a reading device 110 for the identification mark on the surface of the wafer can be mounted. The sixth mount position 26 is an opening with respect to which the device or the inspection of the wafer edge is mounted in such a way that the illumination and the light reflected from the wafer edge reach the camera 115$_K$. The second board 12 of the assembly unit 10 exhibits a mount position 20 for the second camera. Also several holes or recesses 201, respectively, are provided for mounting the first camera. The reinforcement element 16, which is immediately opposite the second camera or the first camera, respectively, exhibits plural openings 202, through which access with calibration tools to the first camera or the second camera, respectively, is possible. This is advantageous, as it is not necessary to remove or disassemble the assembly unit 10 for calibration.

Figure 14:
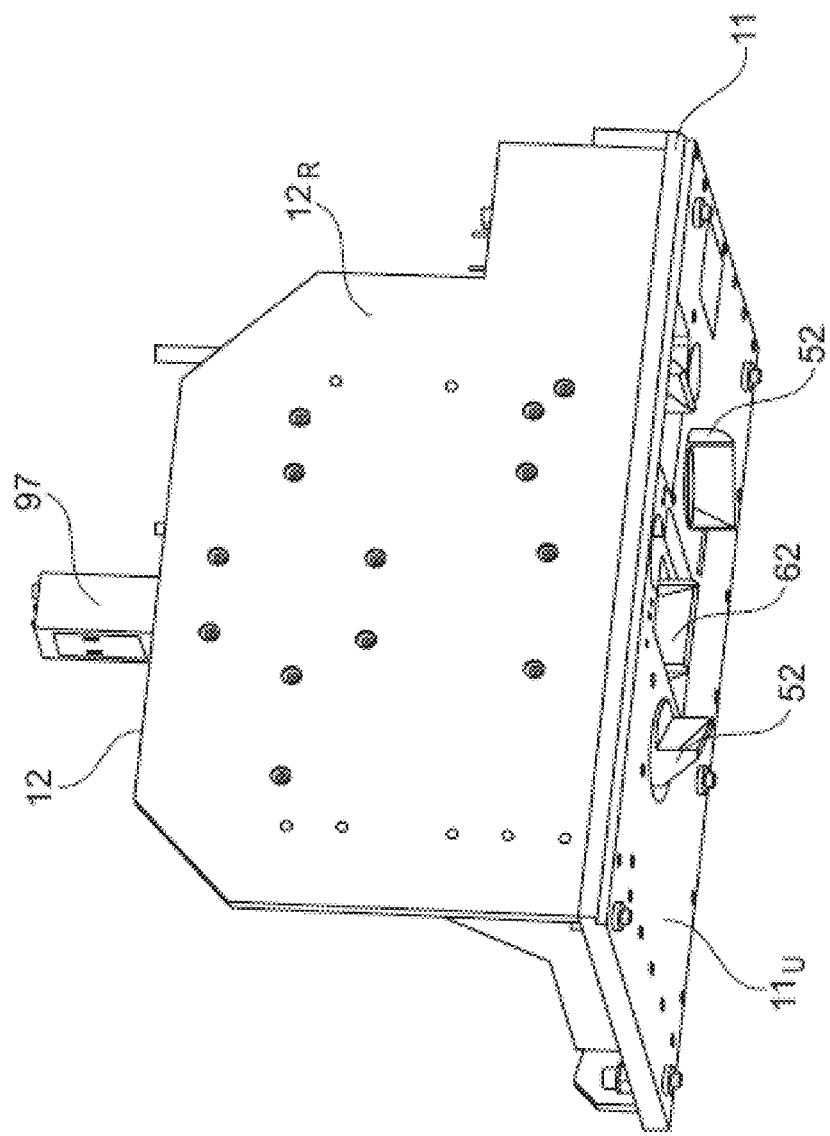
FIG. 14 shows a perspective view of the assembly unit, wherein also the tilted mirror elements, extending below the assembly unit, for the individual illumination systems are visible.

FIG. 14 is a perspective view of the assembly unit 10, wherein the bottom side 11$_U$ of the first board 11 is visible. In the representation shown in FIG. 4, the rear side 12$_R$ of the second board 12 is in view. Plural tilted mirrors 52, 62 reach beyond the bottom side 11$_U$ of the first board 11, which are provided to direct light from the illumination systems for the dark field illumination onto the surface of the wafer under the respectively set angles.

Figure 15:
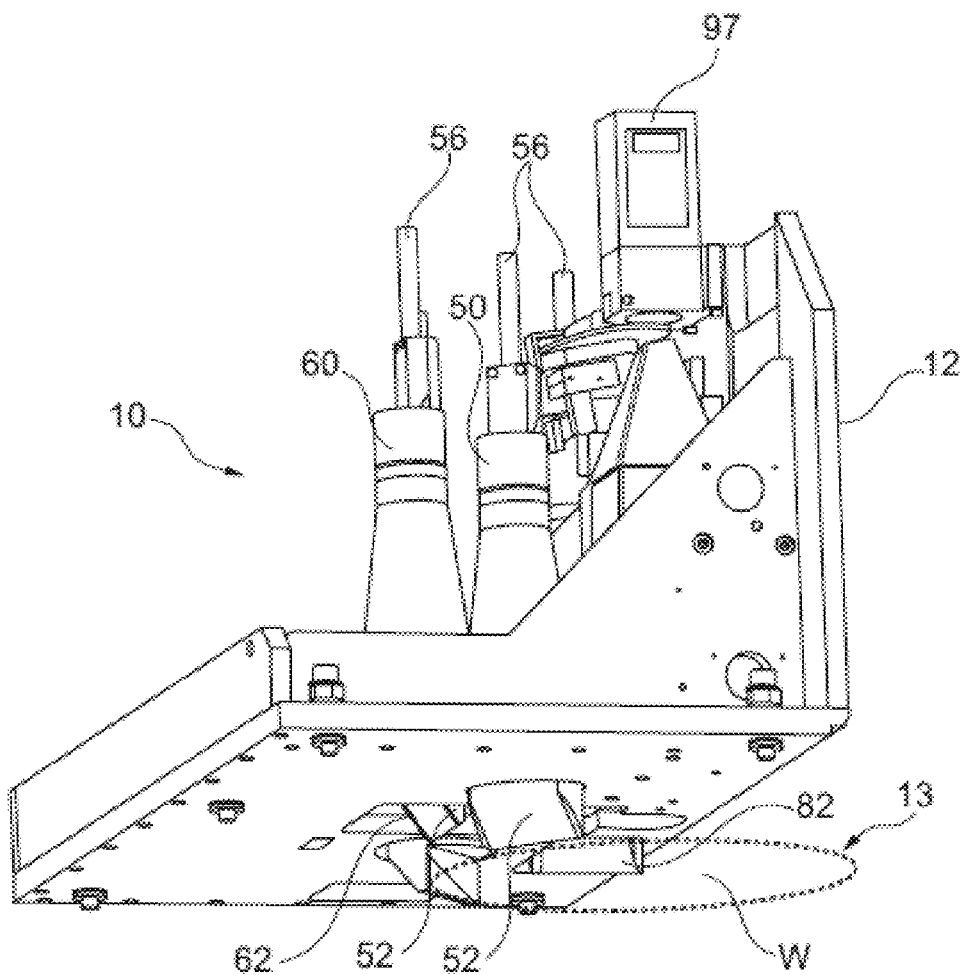
FIG. 15 shows a perspective side view of the assembly unit with a plurality of elements mounted thereon, as well as the tilted mirror elements in correspondence with a wafer to be inspected.

FIG. 15 also is a perspective view of the assembly unit 10, wherein the spatial arrangement of the optical elements 52, 62 is shown. The optical elements 52, 62 are tilted mirrors, which direct the light for the dark field illumination onto the surface 13 of the wafer W. As has already been mentioned in the description of FIG. 14, the tilted mirrors 52, 62 extend beyond the bottom side 11$_U$ of the first board 11 of the assembly unit 10. In the representation of the assembly unit 10 shown in FIG. 15 only the first camera 97 is mounted on the second board 12. In addition to the first camera 97 the optical elements 60 and 50 are shown, which are responsible for the dark field illumination of the surface 13 of the wafer W. As already mentioned, the light for the dark field illumination is provided from the light sources, which are flash lights 120, via optical fibres 56.

Figure 16:
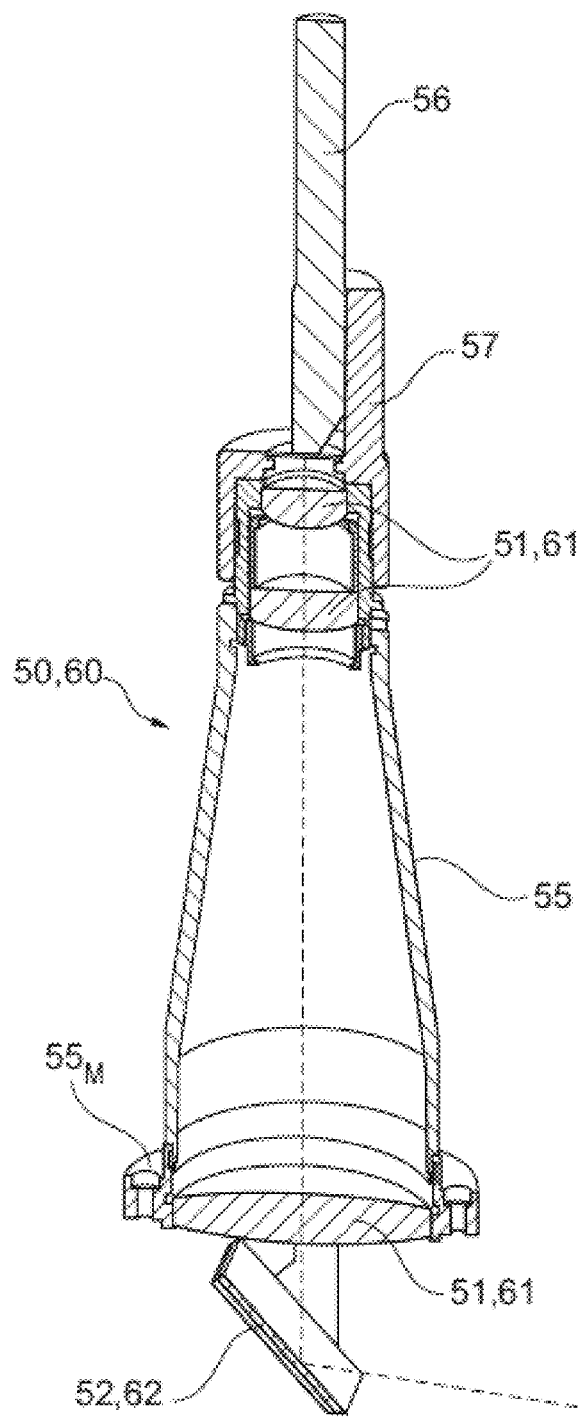
FIG. 16 shows a section of one of the casings, which carries plural optical elements, which are mounted on the assembly unit.

FIG. 16 shows a first embodiment of an optical element 50 for the dark field illumination of the surface of the wafer. The optical element 50 comprises a casing 55, into which the imaging optical elements 51 are mounted. Light from the light sources, which are flash lights 120, is transmitted to the optical unit 50 through an optical fibre 56. The optical fibre 56 is connected to the optical element 50 for the dark field illumination by a fibre connector 57 The optical element 50 for the dark field illumination exhibits a ring mount 50$_M$, by which the optical element 50 can be mounted as a unit on the first board 11 of the assembly unit 10 at the correspondingly provided mount positions. Furthermore the optical element 50 for the dark field illumination carries a tilted mirror 52, which directs light onto the surface of the wafer under a defined angle. The imaging optical elements 51 of the optical element 50 for the dark field illumination are of such design that the illumination of the surface of the wafer is telecentric.

Figure 17:
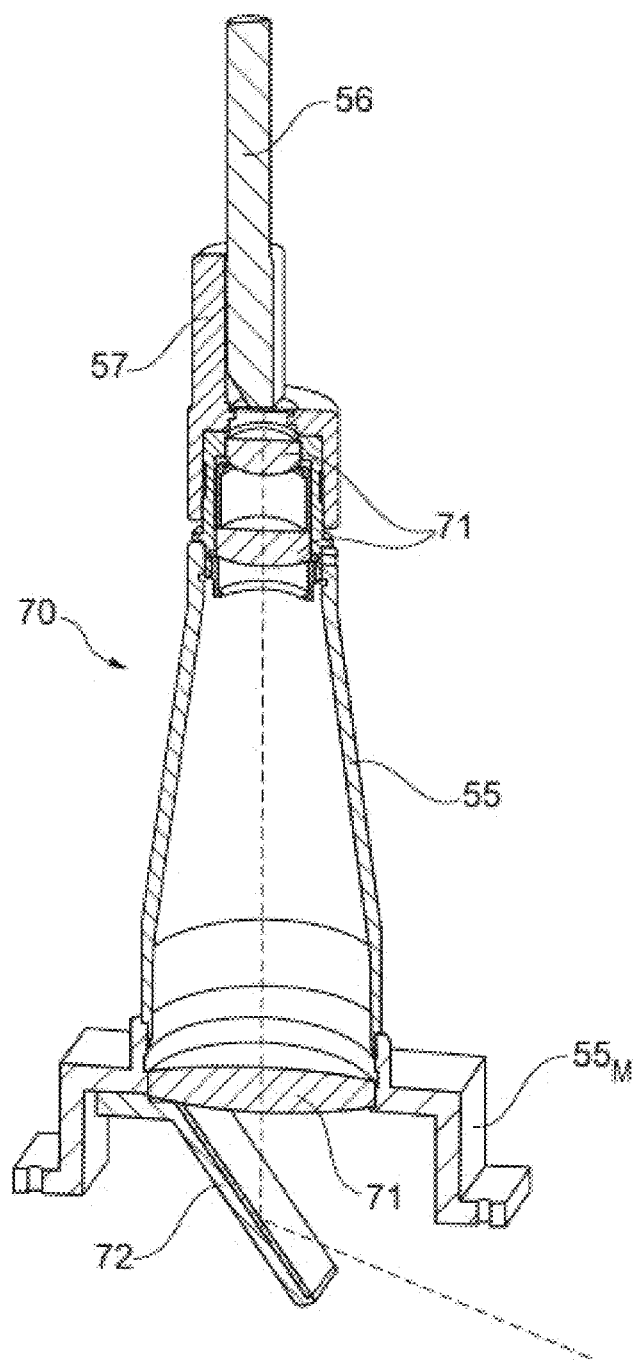
FIG. 17 shows a further embodiment of a casing with the respectively corresponding optical elements to be mounted on the assembly unit.

FIG. 17 shows a further embodiment of the optical element 70 for the dark field illumination of the surface of the wafer. The imaging optical elements 71 of the optical element 70 for the dark field illumination are also housed in a casing 55. Light from the light sources also is supplied to the casing 55 or to the imaging optical elements 71 of the optical element 70 for the dark field illumination, respectively, through an optical fibre 56, which terminates in a fibre connector 57 The casing 55 is located in a mounting element 55$_M$, which also carries the tilted mirror 72, which directs the light under a defined angle onto the surface of the wafer. Here, also, all imaging optical elements 71 are of such design that telecentric illumination of the surface of the wafer is possible. The optical element 70 for the dark field illumination can be mounted at a correspondingly provided mount position on the first board 11 of the assembly unit 10 by the mounting element 55$_M$.

The embodiments of the optical elements 50 and 70, respectively, for the dark field illumination shown in FIGS. 16 and 17 have the advantage that they can be attached to the first board 11 of the assembly unit 10 as pre-assembled units. In addition the mount positions on the first board 11 of the assembly unit 10 are designed in such a way that the optical units 50, 60, 70, and 80 can be mounted at the various mount position on the first board 11, according to the respective measurement problem. Mounting the optical elements 50, 60, 70, and 80 already amounts to a pre-calibration of the optical elements 60, 70, and 80. Thus after retrofitting of the apparatus for the inspection of the surface of a wafer, measurements can commence again quickly. The pre-calibration and the mount positions of essentially like design for the optical elements 50, 60, 70, and 80, give rise to a plug-and-play capability.

Figure 18:
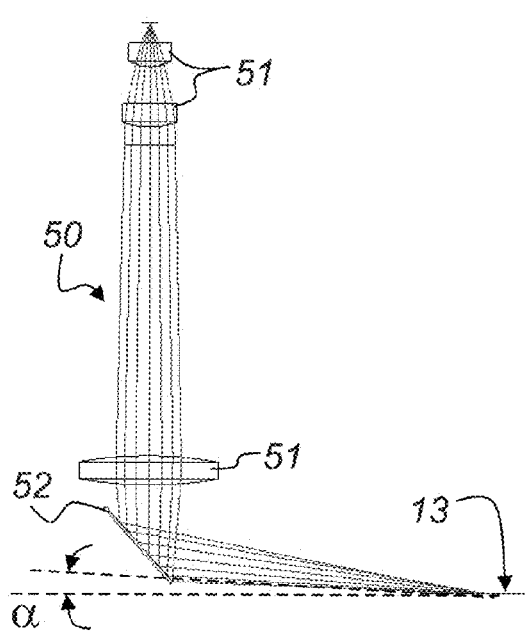
FIG. 18 shows the light path defined by the optical elements in order to achieve dark field illumination of the surface of the wafer under an angle of 6.5°.

FIG. 18 shows the arrangement of the imaging optical elements 51 of the optical unit 50, wherein light for the dark field illumination impinges onto the surface 13 of the wafer W under an angle $\alpha=6.5°$. The angle shown in FIG. 18 only is a choice from within an interval. The tilted mirror 52 is arranged in such a way that the light for the dark field illumination impinges on the surface 13 of the wafer W with the required inclination. The optical unit 50 shown in FIG. 18 is mounted at the first mount position 21 and at the second mount position 22 on the assembly unit 10 in such a way that the light from the dark field illumination encloses an angle of 45° with the X-coordinate direction of the dies arranged on the surface 13 of the wafer W or with the X-coordinate direction of the surface of the blank wafer.

Figure 19:
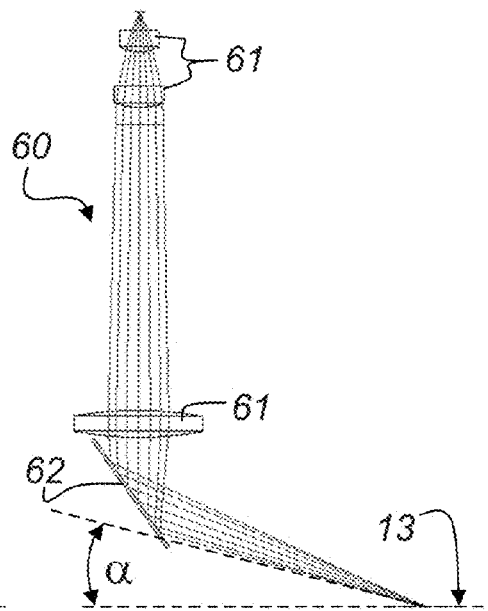
FIG. 19 shows the light path defined by the optical elements in order to achieve a dark field illumination of the surface of the wafer, which impinges on the surface of the wafer under an angle of about 20°.

FIG. 19 shows a further embodiment of the optical unit 60 for the dark field illumination, which is designed in such a way that light impinges onto the surface 13 of the wafer W under an angle $\alpha$ of 20°. The angle shown in FIG. 19 only is a choice from within an interval. The tilted mirror 62 of the optical unit 60 is arranged in such a way that the angle of incidence $\alpha$ of 20° can be achieved. The optical unit 60 for the dark field illumination is mounted at the third mount position on the first board 11 of the assembly unit 10 in such a way that the propagation of light from the third mount position is orthogonal to the X-coordinate direction of the dies arranged on the surface 13 of the wafer W or orthogonal to the X-coordinate direction of the surface of the blank wafer.

Figure 20:
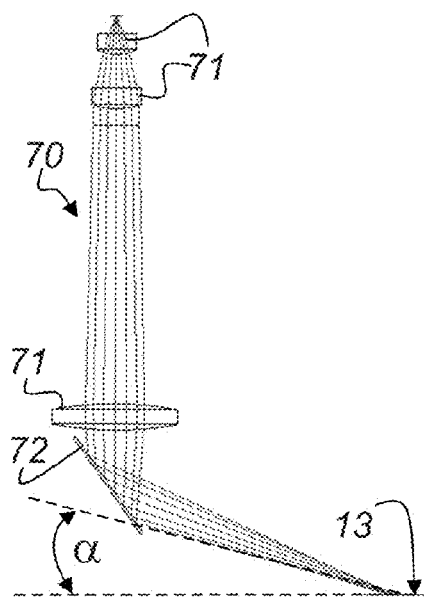
FIG. 20 schematically shows the light path through the optical elements for the dark field illumination, wherein the dark field illumination impinges on the surface of the wafer under an angle of 30°.

FIG. 20 shows a further embodiment of an optical unit 70, which is essentially identical with the optical unit of FIG. 19. The tilted mirror 72, here, too, is arranged in such a way that the light from the dark field illumination impinges onto the surface 13 of the wafer under an angle $\alpha$ of 20°. The angle shown in FIG. 20 only is a choice from within an interval. The optical unit 70 is mounted at the fourth mount position on the first board 11 of the assembly unit 10 in such a way that the propagation of light from the fourth mount position is parallel to the X-coordinate direction of the dies arranged on the surface 13 of the wafer W.

Figure 21:
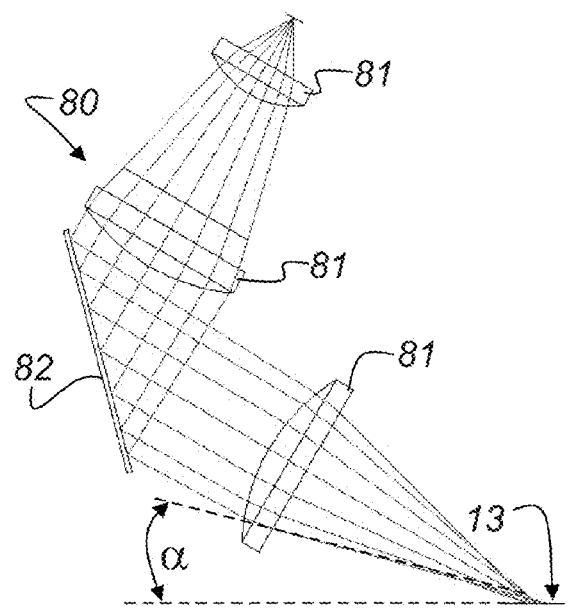
FIG. 21 schematically shows the light path wherein the illumination for the dark field illumination impinges on the surface of the wafer under an angle of about 30°.

FIG. 21 shows a further embodiment of the optical unit 80 for the dark field illumination. The tilted mirror 82 is arranged in such a way that the light impinges onto the surface 13 of the wafer W under an angle of 30°. The angle shown in FIG. 21 only is a choice from within an interval. The imaging optical elements 81 of the optical unit 80 are also housed in a casing (not shown), in order that as much as possible of the light from the light source reaches the surface 13 of the wafer. The optical unit 80 shown in FIG. 21 essentially is suitable for the required dark field illumination of rather deep structures on the surface 13 of the wafer and for the corresponding imaging of the structures with the first camera 97 or the second camera 98.

The optical units 50, 60, 70, and 80, with their imaging optical elements 51, 61, 71, and 81, shown in FIGS. 18 to 21 are of such design that the illumination path for the dark field illumination is telecentric. Telecentricity is of particular importance to achieve the necessary image quality for the dark field illumination and imaging, respectively. The apparatus for the optical inspection of a wafer primarily records the dies arranged on the surface of the wafer and exhibiting a plurality of structures. The structures of the dies vary with respect to their response to the incident light. This variance in response cannot be eliminated, so there is need to assure that no further variance of the response is introduced by the light for the illumination of the structures to be imaged. This can only be assured by designing the imaging optical elements 51, 61, 71, and 81 of the optical units 50, 60, 70, and 80 for the respective dark field illuminations in such a way that a telecentric illumination of the surface 13 of the wafer W is provided by them.

Figure 22:
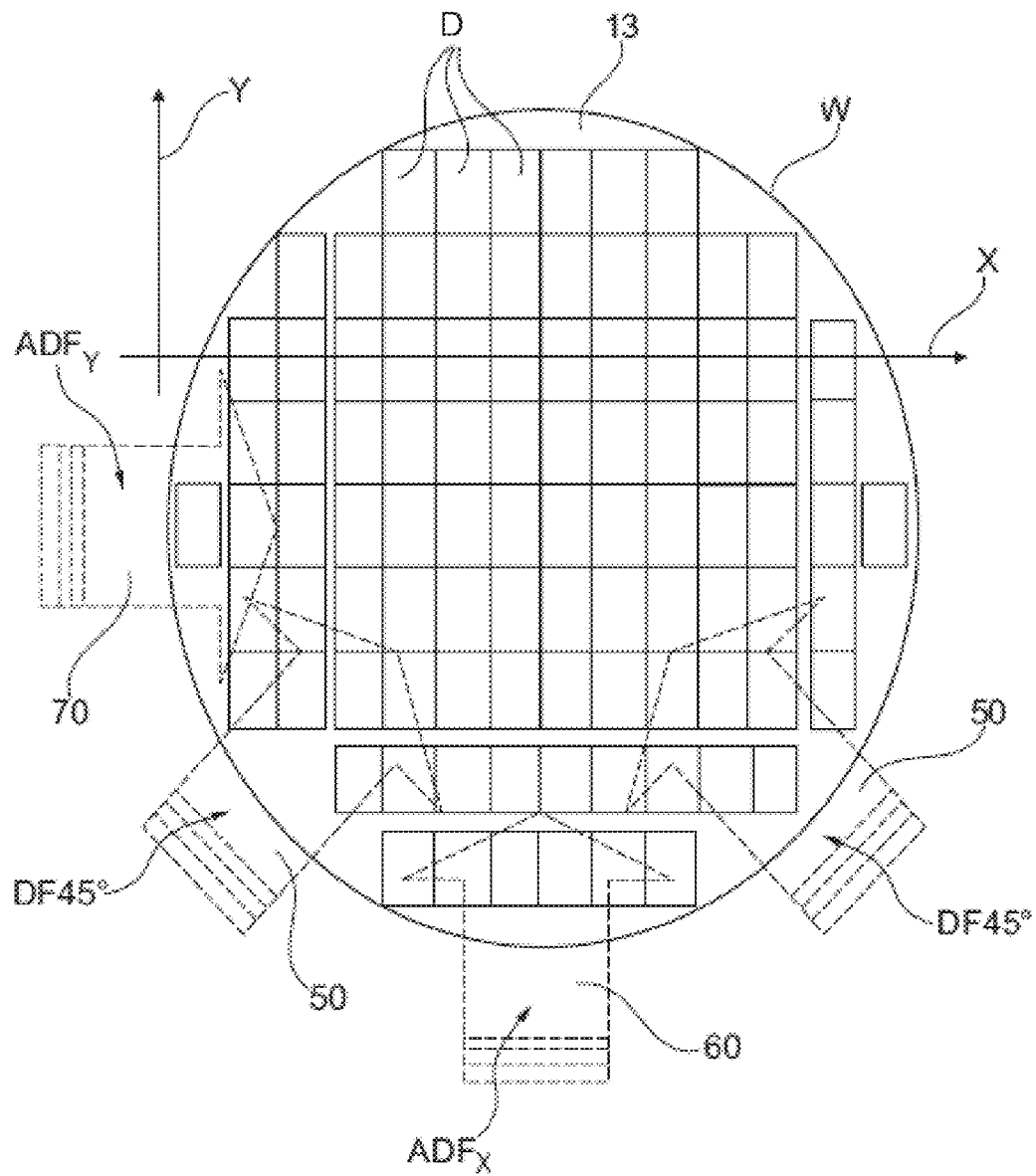
FIG. 22 shows the arrangement of the various dark field illuminations with respect to the orientation of the dies on the surface of the wafer.

FIG. 22 schematically shows an arrangement of the various dark field illuminations with respect to the surface 13 of the wafer W. As already mentioned, a plurality of dies D are arranged on the surface 13 of the wafer W. For the optical inspection the wafer is placed with a defined orientation on the table movable in the X- and in the Y-coordinate direction. The dies D on the surface 13 of the wafer W therein are aligned with the X-coordinate direction and with the Y-coordinate direction. Two optical units 50 (see FIG. 16) are each arranged under an angle of 45° with respect to the orientation of the dies D on the surface of the wafer. The optical unit 60, as shown in FIG. 16, is arranged in such a way that it directs light orthogonally to the dies D arranged in X-coordinate direction on the surface 13 of the wafer W. The second dark field illumination 70 is arranged in such a way with respect to the dies D that it directs light parallel to the X-coordinate direction onto the surface 13 of the wafer W. The two dark field illuminations, which are oriented orthogonally to the X-coordinate direction and in parallel to the X-coordinate direction, respectively, are referred to a $ADF_X$ (Advanced Dark Field) and as $ADF_Y$ (Advanced Dark Field).

Figure 23:
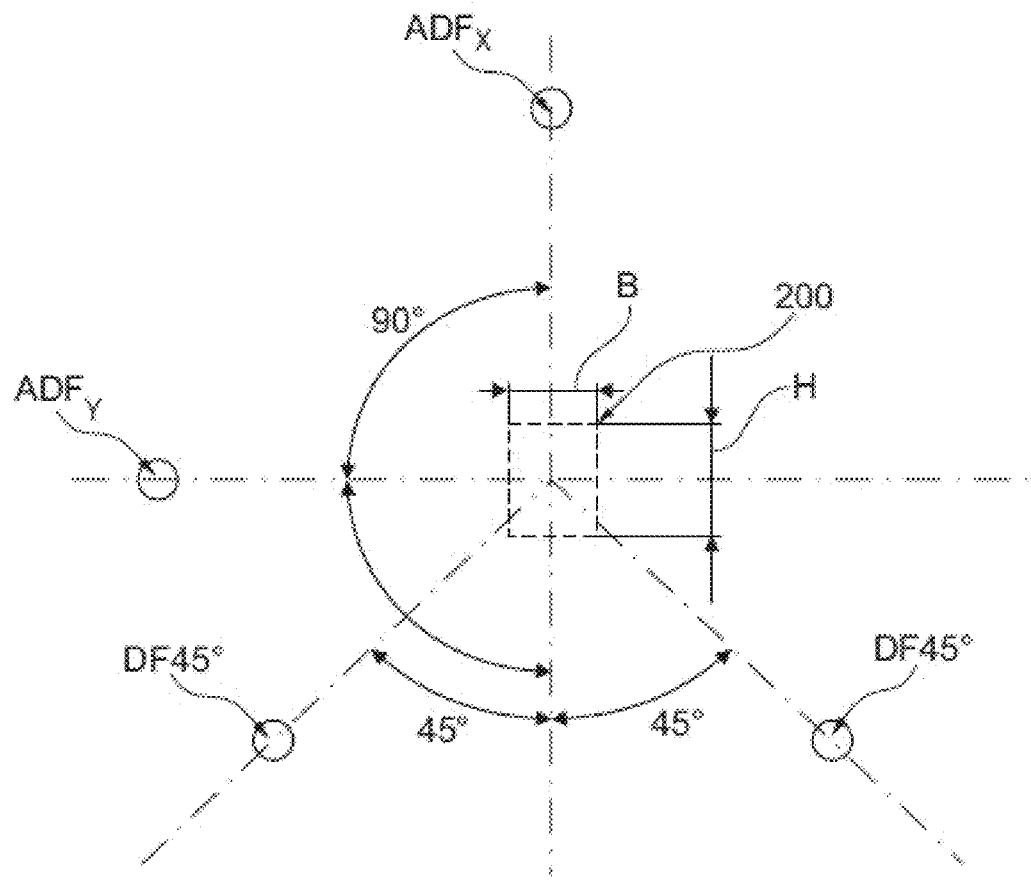
FIG. 23 also shows the arrangement of the individual illuminations for the dark field illumination with respect to the orientation of the illuminated area on the surface of the wafer.

FIG. 23 again schematically shows the arrangement of the various illuminations for the dark field illumination with respect to an illuminated area 200, which has a height H and a width B. As already mentioned, the two illuminations for the Advanced Dark Field ($ADF_X$ and $ADF_Y$) enclose an angle of 90° between them. In a corresponding fashion the dark field illuminations, which enclose an angle of 45° with the dies D arranged on the surface 13 of the wafer W, enclose an angle of 90° between them. All dark field illuminations of the surface 13 of the wafer are designed in such a way that they illuminate a single illuminated area 200. An illuminated area 200 of preferred size has a height of 30.7 mm and a width of 23 mm.

Figure 24:
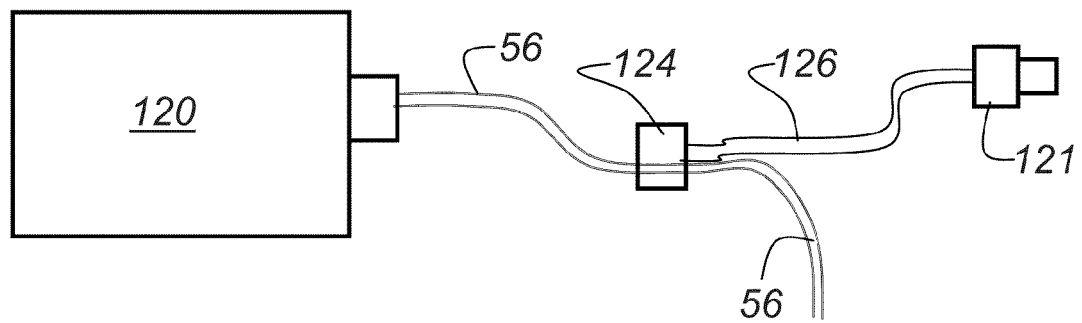
FIG. 24 shows a possibility for coupling out part of the light coming from the light source and guided in an optical fibre.

FIG. 24 schematically shows an embodiment for coupling out part of the light from an optical fibre 56 cooperating with a respective light source 120, in order to transmit the light coupled out to a detection system (not shown). Both the intensity and the spectral composition of the light from the flash light 120 are monitored, and if necessary corrected, by the detection system. This is necessary in order to achieve a sufficient quality of inspection of the surface of the wafer. Thus it is assured that the surface of the wafer is illuminated with light of constant intensity and constant spectral composition. The intensity and the spectral composition of the individual light pulses from the flash lights 120 show slight variations from pulse to pulse, so that these variations need to be determined in order to make adjustments to the flash lights, if necessary, or to eventually eliminate the variations mathematically during the evaluation of the images captured from the surface of the wafer. In order to couple out part of the light from the optical fibre 56, a coupling-out interface 124 is provided on the optical fibre. A further optical fibre 126 connects the coupling-out interface 124 with the detection system. At the free end of the further optical fibre 126 a fibre connector 121 is provided, to facilitate optical coupling to the detection system.

Figure 25:
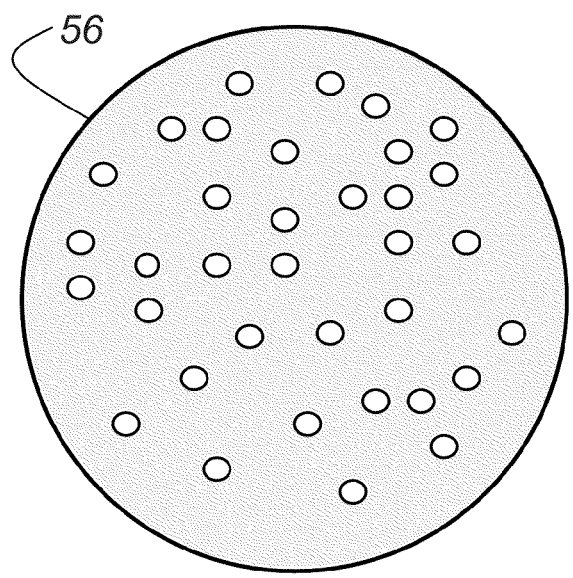
FIG. 25 shows a schematic representation of the cross section of an optical fibre according to the invention.

FIG. 25 shows a cross section of the optical fibre 56. The light from the flash lights 120 is statistically distributed in the cross section of the optical fibre 56.

Figure 26:
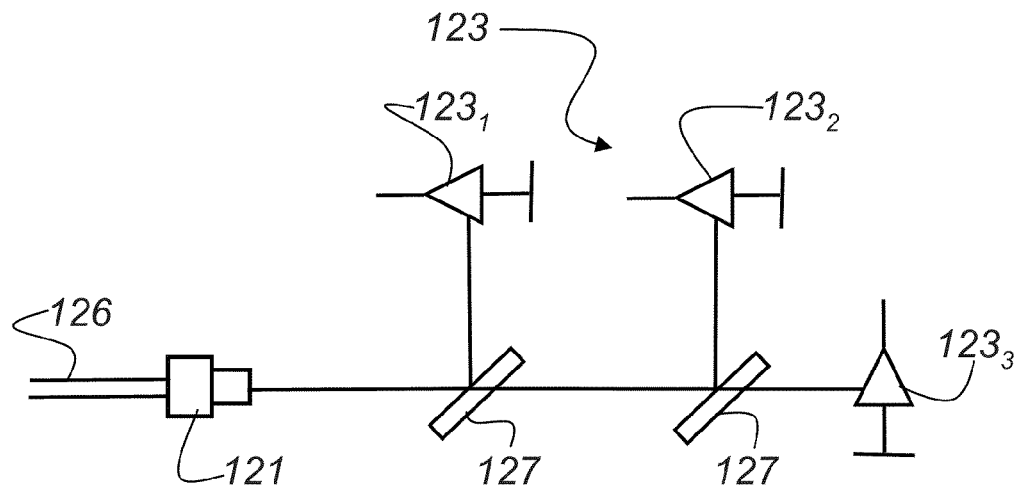
FIG. 26 shows the arrangement of the fibre connector of the coupling-out interface with three diodes for the determination of the intensity of the individual spectral components of light from the light source.

FIG. 26 shows a first embodiment of the detection system 123. The detection system 123 consists of three diodes $123_1$, $123_2$, and $123_3$. The light exiting the further optical fibre 126 at the fibre connector 121 is directed onto the respective diodes $123_1$, $123_2$, and $123_3$ by two dichroic beam splitters 127. Different spectral components of the light from the flash lights 120 can be directed onto the three diodes $123_1$, $123_2$, and $123_3$ by the dichroic beam splitters 127.

Figure 27:
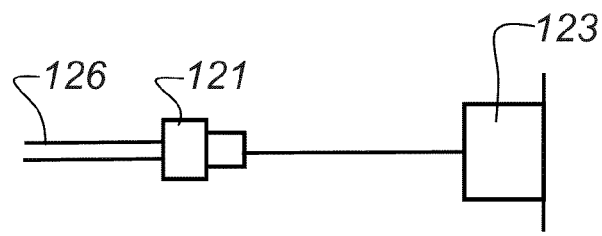
FIG. 27 shows the arrangement of the fibre connector of the coupling-out interface and diode, by which the intensity of at least three spectral components can be determined.

A further embodiment for the detection of the light from the flash lights 120 is shown in FIG. 27. The light exiting the further optical fibre 126 at the fibre connector 121 reaches a single diode 123, which is a three-quadrant diode.

Figure 28:
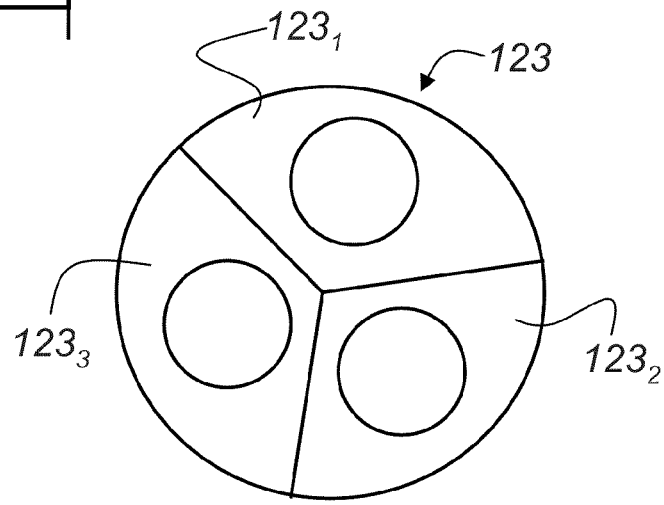
FIG. 28 shows a top view of the diode, by which the three spectral components of light can be determined.

FIG. 28 shows a top view of the diode 123. The diode 123, which is the detection system in this embodiment, in a first quadrant $123_1$ comprises a first diode, in a second quadrant $123_2$ comprises a second diode, and in a third quadrant $123_3$ comprises a third diode. Both the fluctuations in intensity and the spectral composition of the light from the flash lights 120 can be determined with the three-quadrant diode.

Figure 29:
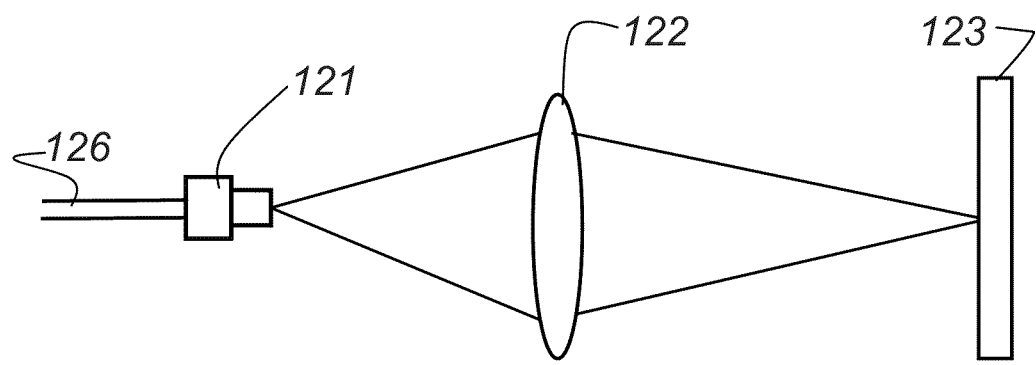
FIG. 29 shows the arrangement of a fibre connector of the coupling-out interface and an area detector, onto which the light exiting the fibre connector is imaged.

FIG. 29 shows a further embodiment of the detection system 123. The light exiting the further optical fibre 126 at the fibre connector 121 is imaged onto the detection system 123 by an imaging element 122. The detection system 123 in this embodiment is an area detector.

Figure 30:
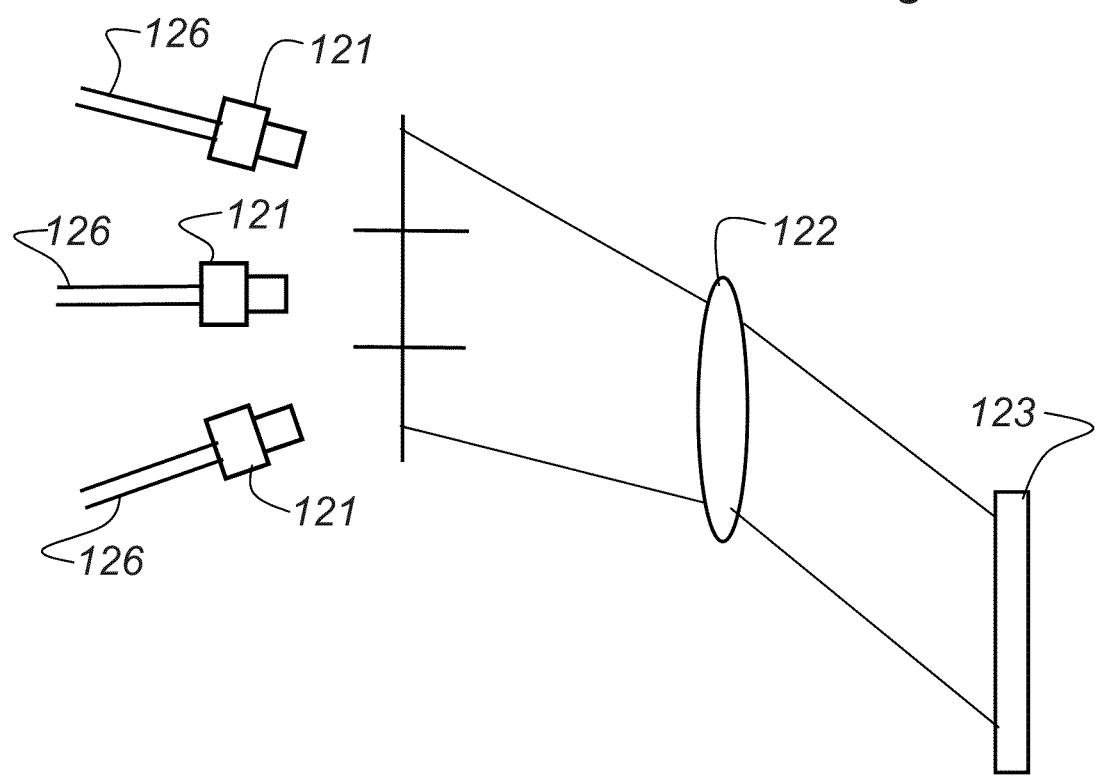
FIG. 30 shows a schematic arrangement, wherein light from three light sources is coupled out and respectively imaged onto an area detector.

In a further embodiment of the invention, shown in FIG. 30, the detection system 123 cooperates with plural fibre connectors 121, which transfer light from plural coupling-out interfaces guided in further optical fibres 126 to the detection system 123. The detection system 123 is an area detector, too. Light from the plural fibre connectors 121 is imaged onto the area detector 123 by the imaging element 122. The embodiment shown here allows to determine the fluctuations in intensity and the spectral composition of several flash lights 120 with a single area detector 123. The light from the plural fibre connectors 121 is directed onto respectively different regions of the area detector 123.

The present invention has been described with reference to preferred embodiments in order to design an apparatus for the optical inspection of the surface of a wafer in such a way that a reliable high quality detection of the surface of the wafer is possible. Independently of that alterations and modifications of individual elements of the apparatus for the optical inspection of the surface of the wafer are possible, without leaving the scope of the subsequent claims.

What is claimed is:

1. An apparatus for optical inspection of wafers, comprising:
   an assembly unit carrying optical elements of at least one illumination path for bright field illumination, optical elements of at least one illumination path for dark field illumination, and several optical elements of at least a first detection path and a second detection path;
   a plurality of corresponding light sources providing the bright field illumination and/or the dark field illumination;
   an imaging optical element of the at least one illumination path for the bright field illumination; and
   a plurality of imaging optical elements of the at least one illumination path for the dark field illumination, wherein the imaging optical elements of the at least one illumination path for the dark field illumination are set into a respective casing, and to each casing corresponds a tilted mirror as an optical element directing the dark field illumination onto a surface of a wafer at a defined angle, each tilted mirror extending below a bottom of a first board of the assembly unit, and
   a plurality of imaging optical elements of the at least one first detection path and second detection path,
   wherein the imaging optical element of the at least one illumination path for the bright field illumination, the plurality of imaging optical elements of the at least one illumination path for the dark field illumination, and the plurality of imaging optical elements of the at least one first detection path and second detection path are designed so that all illumination paths and all detection paths are telecentric.

2. The apparatus of claim 1, wherein one of the optical elements in the illumination path is a mount with at least two different changeable positions for filter elements, so that the spectral composition of light in the illumination path is settable.

3. The apparatus of claim 1, wherein one of the optical elements in the first detection path is a first camera, which is provided with an objective as an imaging optical element, and a field lens is provided as an imaging optical element in the first detection path, the field lens being located in front of a spectrally selective output coupling means.

4. The apparatus of claim 3, wherein in the first detection path between the objective of the first camera and the field lens a respective element is located, which exhibits at least two different positions for filter elements.

5. The apparatus of claim 3, wherein the spectrally selective output coupling means couples a portion of the light in the first detection path into the second detection path, in which a second camera with an objective is provided as an imaging optical element.

6. The apparatus of claim 1, wherein light from the light sources, which are flash lights, is delivered to each casing of the at least one illumination path for a dark field illumination through an optical fibre, and wherein the optical fibre is connected with the casing via a fibre connector.

7. The apparatus of claim 1, wherein the optical elements for the bright field illumination and the optical elements for the dark field illumination are designed in such a way that a rectangular illuminated area is provided on the surface of the wafer, wherein the illumination of the illuminated area is homogeneous.

8. The apparatus of claim 1, wherein the assembly unit is located in the apparatus above a table which is movable in a X-coordinate direction and in a Y-coordinate direction and which carries the wafer and wherein the assembly unit is constructed of a first board and a second board, the first board exhibiting an orientation essentially parallel to the surface of the wafer and the second board being connected orthogonally to the first board.

9. The apparatus of claim 8, wherein the first board is connected to the second board by reinforcement elements and wherein a further reinforcement element, which is parallel to the second board, divides the first board into a first section and a second section.

10. The apparatus of claim 9, wherein the first board essentially carries the plural optical elements of the at least one illumination path of the dark field illumination.

11. The apparatus of claim 10, wherein the first board exhibits a first, a second, a third and a fourth mount position, wherein at the first mount position and at the second mount position the respective casing of the optical elements is mounted, so that a direction of propagation of light from the first mount position and the second mount position encloses an angle of 45° with an X-coordinate direction of the surface of the wafer, wherein at the third mount position the casing for the optical elements is mounted, so that a direction of propagation of light from the third mount position is perpendicular to the X-coordinate direction of the surface of the wafer, and wherein at the fourth mount position the casing for the optical elements is mounted, so that a direction of propagation of light from the fourth mount position is parallel to the X-coordinate direction of the surface of the wafer.

12. The apparatus of claim 1, wherein a detection system is provided, by which the intensity of light from the individual light sources, which are flash lights, is determinable and settable.

13. The apparatus of claim 12, wherein the light from each of the flash lights is guided by a respective optical fibre, and wherein the optical fibre exhibits a coupling-out interface, from where a portion of the light from the respective flash light is transmittable to the detection system.

14. The apparatus of claim 13, wherein a further optical fibre is connected with the coupling-out interface, the further optical fibre exhibiting a fibre connector at its free end, by which the light coupled out is transmittable to the detection system.

15. The apparatus of claim 14, wherein the light exiting the fibre connector is transmittable to three different diodes which form the detection system by two dichroic beam splitters.

16. The apparatus of claim 14, wherein the light exiting the fibre connector is transmittable to a diode with three quadrants, which form the detection system.

17. The apparatus of claim 14, wherein the light exiting the fibre connector is imageable by an imaging element onto an area detector, which forms the detection system.

18. The apparatus of claim 14, wherein the light exiting from plural fibre connectors is imageable onto an area detector by an imaging element in such a way that the light from different fibre connectors impinges on different regions of the area detector, wherein the area detector forms the detection system.

19. An apparatus for optical inspection of wafers, comprising:
   an assembly unit which carries optical elements of at least one illumination path for a bright field illumination and optical elements of at least one illumination path for a dark field illumination and the assembly unit carries several optical elements of at least a first detection path and a second detection path;
   a plurality corresponding light sources provide the bright field illumination and/or the dark field illumination; an imaging optical element of the at least one illumination path for the bright field illumination; and
   a plurality of imaging optical elements of the at least one illumination path for the dark field illumination, and a plurality of imaging optical elements of the at least one first detection path and second detection path, wherein the imaging optical element of the at least one illumination path for the bright field illumination, the plurality of imaging optical elements of the at least one illumination path for the dark field illumination and the plurality of imaging optical elements of the at least one first detection path and second detection path are designed in such a way that all illumination paths and all detection paths are telecentric;
   wherein the assembly unit is located in the apparatus above a table which is movable in a X-coordinate direction and in a Y-coordinate direction and which carries the wafer and wherein the assembly unit is constructed of a first board and a second board, the first board exhibiting an orientation essentially parallel to the surface of the wafer and the second board being connected orthogonally to the first board;
   wherein the first board is connected to the second board by reinforcement elements and wherein a further reinforcement element, which is parallel to the second board, divides the first board into a first section and a second section; and
   wherein the second board essentially carries the plural optical elements of the at least one first detection path and the at least one second detection path and the plural optical elements of the at least one illumination path for the bright field illumination.

20. An apparatus for optical inspection of wafers, comprising:
   an assembly unit which carries optical elements of at least one illumination path for a bright field illumination and optical elements of at least one illumination path for a dark field illumination and the assembly unit carries several optical elements of at least a first detection path and a second detection path;
   a plurality corresponding light sources provide the bright field illumination and/or the dark field illumination; an imaging optical element of the at least one illumination path for the bright field illumination; and
   a plurality of imaging optical elements of the at least one illumination path for the dark field illumination, and a plurality of imaging optical elements of the at least one first detection path and second detection path, wherein the imaging optical element of the at least one illumination path for the bright field illumination, the plurality of imaging optical elements of the at least one illumination path for the dark field illumination and the plurality of imaging optical elements of the at least one first detection path and second detection path are designed in such a way that all illumination paths and all detection paths are telecentric;
   wherein the assembly unit is located in the apparatus above a table which is movable in a X-coordinate direction and in a Y-coordinate direction and which carries the wafer and wherein the assembly unit is constructed of a first board and a second board, the first board exhibiting an orientation essentially parallel to the surface of the wafer and the second board being connected orthogonally to the first board; and
   wherein the second board carries at least the first camera, exhibits a mount position for an optional second camera, carries the imaging optical element of the at least one illumination path for the bright field illumination, carries the field lens in such a way that it is part both of the first and the second detection path, carries plural elements, which exhibit at least two different, changeable positions for filter elements, and carries a casing for the bright field illumination.

21. An apparatus for optical inspection of wafers, comprising:
   an assembly unit which carries optical elements of at least one illumination path for a bright field illumination and optical elements of at least one illumination path for a dark field illumination and the assembly unit carries several optical elements of at least a first detection path and a second detection path;
   a plurality corresponding light sources provide the bright field illumination and/or the dark field illumination; an imaging optical element of the at least one illumination path for the bright field illumination; and a plurality of imaging optical elements of the at least one illumination path for the dark field illumination, and a plurality of imaging optical elements of the at least one first detection path and second detection path, wherein the imaging optical element of the at least one illumination path for the bright field illumination, the plurality of imaging optical elements of the at least one illumination path for the dark field illumination and the plurality of imaging optical elements of the at least one first detection path and second detection path are designed in such a way that all illumination paths and all detection paths are telecentric;

wherein the assembly unit is located in the apparatus above a table which is movable in a X-coordinate direction and in a Y-coordinate direction and which carries the wafer and wherein the assembly unit is constructed of a first board and a second board, the first board exhibiting an orientation essentially parallel to the surface of the wafer and the second board being connected orthogonally to the first board;

wherein the first board is connected to the second board by reinforcement elements and wherein a further reinforcement element, which is parallel to the second board, divides the first board into a first section and a second section;

wherein the first board essentially carries the plural optical elements of the at least one illumination path of the dark field illumination;

wherein the first board exhibits a first, a second, a third and a fourth mount position, wherein at the first mount position and at the second mount position the respective casing of the optical elements is mounted, so that a direction of propagation of light from the first mount position and the second mount position encloses an angle of 45° with an X-coordinate direction of the surface of the wafer, wherein at the third mount position the casing for the optical elements is mounted, so that a direction of propagation of light from the third mount position is perpendicular to the X-coordinate direction of the surface of the wafer, and wherein at the fourth mount position the casing for the optical elements is mounted, so that a direction of propagation of light from the fourth mount position is parallel to the X-coordinate direction of the surface of the wafer; and wherein one of the optical elements is a tilted mirror and arranged at a casing in such a way that a central ray of light from the first mount position and from the second mount position of the dark field illumination impinges on the surface of a wafer with an angle between 3° and 10°.

22. An apparatus for optical inspection of wafers, comprising:

an assembly unit which carries optical elements of at least one illumination path for a bright field illumination and optical elements of at least one illumination path for a dark field illumination and the assembly unit carries several optical elements of at least a first detection path and a second detection path;

a plurality corresponding light sources provide the bright field illumination and/or the dark field illumination; an imaging optical element of the at least one illumination path for the bright field illumination; and a plurality of imaging optical elements of the at least one illumination path for the dark field illumination, and a plurality of imaging optical elements of the at least one first detection path and second detection path, wherein the imaging optical element of the at least one illumination path for the bright field illumination, the plurality of imaging optical elements of the at least one illumination path for the dark field illumination and the plurality of imaging optical elements of the at least one first detection path and second detection path are designed in such a way that all illumination paths and all detection paths are telecentric;

wherein the assembly unit is located in the apparatus above a table which is movable in a X-coordinate direction and in a Y-coordinate direction and which carries the wafer and wherein the assembly unit is constructed of a first board and a second board, the first board exhibiting an orientation essentially parallel to the surface of the wafer and the second board being connected orthogonally to the first board;

wherein the first board is connected to the second board by reinforcement elements and wherein a further reinforcement element, which is parallel to the second board, divides the first board into a first section and a second section;

wherein the first board essentially carries the plural optical elements of the at least one illumination path of the dark field illumination;

wherein the first board exhibits a first, a second, a third and a fourth mount position, wherein at the first mount position and at the second mount position the respective casing of the optical elements is mounted, so that a direction of propagation of light from the first mount position and the second mount position encloses an angle of 45° with an X-coordinate direction of the surface of the wafer, wherein at the third mount position the casing for the optical elements is mounted, so that a direction of propagation of light from the third mount position is perpendicular to the X-coordinate direction of the surface of the wafer, and wherein at the fourth mount position the casing for the optical elements is mounted, so that a direction of propagation of light from the fourth mount position is parallel to the X-coordinate direction of the surface of the wafer; and wherein one of the optical elements is tilted minor and arranged at a casing in such a way that a central ray of light from the third mount position and the fourth mount position of the dark field illumination impinges on the surface of the wafer with an angle between 15° and 25°.

23. The apparatus of claim 22, wherein the casing for the optical elements at the third mount position is exchangeable for a casing for the optical elements wherein one of the optical elements is a tilted mirror being arranged in such a way that a central ray of light from the third mount position impinges on the surface of a wafer with an angle between 20° and 40°.

24. An apparatus for optical inspection of wafers, comprising:

an assembly unit which carries optical elements of at least one illumination path for a bright field illumination and optical elements of at least one illumination path for a dark field illumination and the assembly unit carries several optical elements of at least a first detection path and a second detection path;

a plurality corresponding light sources provide the bright field illumination and/or the dark field illumination; an imaging optical element of the at least one illumination path for the bright field illumination; and a plurality of imaging optical elements of the at least one illumination path for the dark field illumination, and a plurality of imaging optical elements of the at least one first detection path and second detection path, wherein the imaging optical element of the at least one illumination path for the bright field illumination, the plurality of imaging optical elements of the at least one illumination path for the dark field illumination and the plurality of imaging optical elements of the at least one first detection path and second detection path are designed in such a way that all illumination paths and all detection paths are telecentric;

wherein the assembly unit is located in the apparatus above a table which is movable in a X-coordinate direction and in a Y-coordinate direction and which carries the wafer and wherein the assembly unit is constructed of a first board and a second board, the first board exhibiting an orientation essentially parallel to the surface of the wafer and the second board being connected orthogonally to the first board;

wherein the first board is connected to the second board by reinforcement elements and wherein a further reinforcement element, which is parallel to the second board, divides the first board into a first section and a second section;

wherein the first board essentially carries the plural optical elements of the at least one illumination path of the dark field illumination;

wherein the first board exhibits a first, a second, a third and a fourth mount position, wherein at the first mount position and at the second mount position the respective casing of the optical elements is mounted, so that a direction of propagation of light from the first mount position and the second mount position encloses an angle of 45° with an X-coordinate direction of the surface of the wafer, wherein at the third mount position the casing for the optical elements is mounted, so that a direction of propagation of light from the third mount position is perpendicular to the X-coordinate direction of the surface of the wafer, and wherein at the fourth mount position the casing for the optical elements is mounted, so that a direction of propagation of light from the fourth mount position is parallel to the X-coordinate direction of the surface of the wafer; and wherein the first board exhibits a fifth mount position for a reading device provided for evaluating an identification mark on the wafer.

25. An apparatus for optical inspection of wafers, comprising:

an assembly unit which carries optical elements of at least one illumination path for a bright field illumination and optical elements of at least one illumination path for a dark field illumination and the assembly unit carries several optical elements of at least a first detection path and a second detection path;

a plurality corresponding light sources provide the bright field illumination and/or the dark field illumination; an imaging optical element of the at least one illumination path for the bright field illumination; and a plurality of imaging optical elements of the at least one illumination path for the dark field illumination, and a plurality of imaging optical elements of the at least one first detection path and second detection path, wherein the imaging optical element of the at least one illumination path for the bright field illumination, the plurality of imaging optical elements of the at least one illumination path for the dark field illumination and the plurality of imaging optical elements of the at least one first detection path and second detection path are designed in such a way that all illumination paths and all detection paths are telecentric;

wherein the assembly unit is located in the apparatus above a table which is movable in a X-coordinate direction and in a Y-coordinate direction and which carries the wafer and wherein the assembly unit is constructed of a first board and a second board, the first board exhibiting an orientation essentially parallel to the surface of the wafer and the second board being connected orthogonally to the first board;

wherein the first board is connected to the second board by reinforcement elements and wherein a further reinforcement element, which is parallel to the second board, divides the first board into a first section and a second section;

wherein the first board essentially carries the plural optical elements of the at least one illumination path of the dark field illumination;

wherein the first board exhibits a first, a second, a third and a fourth mount position, wherein at the first mount position and at the second mount position the respective casing of the optical elements is mounted, so that a direction of propagation of light from the first mount position and the second mount position encloses an angle of 45° with an X-coordinate direction of the surface of the wafer, wherein at the third mount position the casing for the optical elements is mounted, so that a direction of propagation of light from the third mount position is perpendicular to the X-coordinate direction of the surface of the wafer, and wherein at the fourth mount position the casing for the optical elements is mounted, so that a direction of propagation of light from the fourth mount position is parallel to the X-coordinate direction of the surface of the wafer; and wherein the first board exhibits a sixth mount position for a device provided for the geometrical alignment of the wafer and for the inspection of the wafer edge.

26. An apparatus for optical inspection of wafers, comprising:

an assembly unit, which carries a plurality of optical elements of an illumination path for a bright field illumination;

a plurality of optical elements of four illumination paths for a dark field illumination;

a plurality of optical elements of a first detection path and a second detection path;

a plurality of flash lights providing light for the bright field illumination and/or dark field illumination via corresponding optical fibres;

an imaging optical element of the at least one illumination path for the bright field illumination;

optical elements of each of the four illumination paths for the dark field illumination and imaging optical elements of the first detection path and the second detection path are designed in such a way that all illumination paths for the bright field illumination and the dark field illumination and the first and second detection paths are telecentric;

a casing for the optical elements of the four illumination paths for the dark field illumination, wherein to the casing corresponds a tilted mirror as an optical element directing the dark field illumination onto a surface of a wafer at a defined angle, each tilted mirror extending below a bottom of a first board of the assembly unit; and several optical fibers configured to transport the light from the flash lights to each of the four illumination paths for dark field illumination via, wherein each optical fibre is connected with the casing by a fibre connector.

27. The apparatus of claim 26, wherein one of the optical elements in the illumination path is a mount with at least two different, changeable positions for filter elements, so that the spectral composition of light in the illumination path is settable.

28. The apparatus of claim 26, wherein a first camera is provided in the first detection path and the first camera having an objective as imaging optical element.

29. The apparatus of claim 26, wherein one of the optical elements in the first detection path is a spectrally selective output coupling means, by which a part of the light in the first detection path optionally is transmittable into the second detection path, in which a second camera having an objective as imaging optical element.

30. An apparatus for optical inspection of wafers, comprising:
an assembly unit, which is located above a table which is movable in a X-coordinate direction and in a Y-coordinate direction and which carries the wafer wherein the assembly unit comprising a first board and a second board, wherein the first board exhibits an orientation essentially parallel to the surface of the wafer and the second board is connected orthogonally to the first board;
optical elements of an illumination path for a bright field illumination,
optical elements of four illumination paths for a dark field illumination set into a respective casing, wherein to each casing corresponds a tilted mirror as an optical element directing the dark field illumination onto a surface of a wafer at a defined angle, each tilted minor extending below a bottom of the first board of the assembly unit; and
plural optical elements of at least a first detection path are carried by the assembly unit;
a plurality of flash lights for providing light for the bright field illumination and/or dark field illumination wherein the light is provided via optical fibres; and
an imaging optical element of the at least one illumination path for the bright field illumination, imaging optical elements of each of the four illumination paths for the dark field illumination, and imaging optical elements of the at least first detection path are designed in such a way that all illumination paths and the at least first detection path are telecentric.

31. The apparatus of claim 30, wherein one of the optical elements in the illumination path is a mount with at least two different, changeable positions for filter elements, so that the spectral composition of light in the illumination path is settable.

32. The apparatus of claim 30, wherein the first board is connected to the second board by reinforcement elements, and wherein a further reinforcement element, which is parallel to the second board, divides the first board into a first section, and a second section.

33. The apparatus of claim 30, wherein the first board carries the optical elements of the four illumination paths, which are respectively located in a casing, and wherein the light from the flash lights is providable to each of the four illumination paths for a dark field illumination via a respective optical fibre, wherein the optical fibre is connected with the casing by a fibre connector.

34. An apparatus for optical inspection of wafers, comprising:
an assembly unit, which is located above a table which is movable in a X-coordinate direction and in a Y-coordinate direction and which carries the wafer wherein the assembly unit consists of a first board and a second board, wherein the first board exhibits an orientation essentially parallel to the surface of the wafer and the second board is connected orthogonally to the first board;
optical elements of an illumination path for a bright field illumination, optical elements of four illumination paths for a dark field illumination and plural optical elements of at least a first detection path are carried by the assembly unit;
a plurality of flash lights for providing light for the bright field illumination and/or dark field illumination wherein the light is provided via optical fibres; and
an imaging optical element of the at least one illumination path for the bright field illumination, imaging optical elements of each of the four illumination paths for the dark field illumination, and imaging optical elements of the at least first detection path are designed in such a way that all illumination paths and the at least first detection path are telecentric;
wherein the second board carries at least the first camera, exhibits a mount position for an optional second camera, carries the imaging optical element of the at least one illumination path for the bright field illumination, carries the field lens in such a way that it is part both of the first detection path and a second detection path, carries plural elements, which exhibit at least two different, changeable positions for filter elements, and carries a casing for the bright field illumination.

35. An apparatus for optical inspection of wafers, comprising:
an assembly unit, which is located above a table which is movable in a X-coordinate direction and in a Y-coordinate direction and which carries the wafer wherein the assembly unit consists of a first board and a second board, wherein the first board exhibits an orientation essentially parallel to the surface of the wafer and the second board is connected orthogonally to the first board;
optical elements of an illumination path for a bright field illumination, optical elements of four illumination paths for a dark field illumination and plural optical elements of at least a first detection path are carried by the assembly unit;
a plurality of flash lights for providing light for the bright field illumination and/or dark field illumination wherein the light is provided via optical fibres; and
an imaging optical element of the at least one illumination path for the bright field illumination, imaging optical elements of each of the four illumination paths for the dark field illumination, and imaging optical elements of the at least first detection path are designed in such a way that all illumination paths and the at least first detection path are telecentric;
wherein at the mount position of the second board a second camera is mounted, wherein the field lens is located in the first detection path and the field lens cooperates both with the first camera and with the second camera.

* * * * *